(12) United States Patent
Stark

(10) Patent No.: US 9,345,589 B2
(45) Date of Patent: May 24, 2016

(54) BONE IMPLANTS FOR ORTHOPEDIC PROCEDURES AND CORRESPONDING METHODS

(71) Applicant: Ilion Medical LLC, Minneapolis, MN (US)

(72) Inventor: John G. Stark, Deephaven, MN (US)

(73) Assignee: Ilion Medical, Inc., Minneapolis, MN (US)

( * ) Notice: Subject to any disclaimer, the term of this patent is extended or adjusted under 35 U.S.C. 154(b) by 68 days.

(21) Appl. No.: 14/135,040

(22) Filed: Dec. 19, 2013

(65) Prior Publication Data
US 2015/0173904 A1    Jun. 25, 2015

(51) Int. Cl.
*A61F 2/30* (2006.01)
*A61F 2/46* (2006.01)

(52) U.S. Cl.
CPC ..... *A61F 2/4644* (2013.01); *A61F 2002/30224* (2013.01); *A61F 2002/30225* (2013.01); *A61F 2002/30227* (2013.01); *A61F 2002/30433* (2013.01); *A61F 2002/30599* (2013.01); *A61F 2002/30611* (2013.01); *A61F 2002/30617* (2013.01); *A61F 2002/30622* (2013.01); *A61F 2310/00359* (2013.01); *Y10T 29/49995* (2015.01)

(58) Field of Classification Search
CPC ..... A61F 2/28; A61F 2/30771; A61F 2/3094; A61F 2002/30224; A61F 2002/30617; A61F 2002/30611; A61F 2002/30622
USPC .............................. 623/17.11–17.16; 606/247
See application file for complete search history.

(56) References Cited

U.S. PATENT DOCUMENTS

| | | | | |
|---|---|---|---|---|
| 5,067,962 | A | * | 11/1991 | Campbell et al. ............. 128/898 |
| 5,192,327 | A | * | 3/1993 | Brantigan .................. 623/17.11 |
| 5,562,669 | A | * | 10/1996 | McGuire .................... 623/13.12 |
| 5,814,084 | A | | 9/1998 | Grivas et al. |
| 5,871,504 | A | * | 2/1999 | Eaton et al. ................... 606/232 |
| 5,895,426 | A | * | 4/1999 | Scarborough et al. ..... 623/17.16 |
| 5,972,368 | A | * | 10/1999 | McKay ............... A61L 27/3608 424/422 |
| 6,099,568 | A | * | 8/2000 | Simonian et al. .......... 623/13.11 |
| 6,200,347 | B1 | * | 3/2001 | Anderson et al. .......... 623/16.11 |

(Continued)

OTHER PUBLICATIONS

University of Michigan (n.d.), "Bone Structure," in BME/ME 456 Biomechanics, retrieved Jul. 19, 2013, from http://www.engin.umich.edu/class/bme456/bonestructure/bonestructure.htm.

(Continued)

*Primary Examiner* — Alvin Stewart
(74) *Attorney, Agent, or Firm* — Dardi & Herbert, PLLC; Peter S. Dardi

(57) ABSTRACT

Implants and procedures for joint fusion make use of implants comprising cortical bone. The implants have lamellae that are generally aligned. In some embodiments, the implants can have indicia that indicate the alignment of the lamellae within the joint. In some embodiments, the implants comprise a plurality of implant elements, with the implant elements oriented so that the lamellae of the elements are aligned with each other. The implants can be inserted into a joint with the lamellae aligned across the joint to resist compression or deforming forces of the joint and to provide for improved implant strength. In some embodiments, the implants can be inserted into a joint over a pin and/or through a cannula to help guide the implant to the implant site within the joint. In some embodiments, the implants can be desirably formed from bone plugs harvested from long bones.

26 Claims, 17 Drawing Sheets

(56) References Cited

U.S. PATENT DOCUMENTS

| | | | |
|---|---|---|---|
| 6,258,125 B1* | 7/2001 | Paul et al. | 623/17.11 |
| 6,328,765 B1* | 12/2001 | Hardwick et al. | 623/23.72 |
| 6,371,988 B1* | 4/2002 | Pafford | A61B 17/1671 606/247 |
| 6,398,811 B1* | 6/2002 | McKay | A61L 27/3658 623/16.11 |
| 6,494,883 B1 | 12/2002 | Ferree | |
| 6,511,509 B1* | 1/2003 | Ford | A61F 2/28 623/23.5 |
| 6,533,802 B2* | 3/2003 | Bojarski et al. | 606/232 |
| 6,579,295 B1* | 6/2003 | Supinski | 623/13.14 |
| 6,595,998 B2* | 7/2003 | Johnson et al. | 606/90 |
| 6,632,247 B2* | 10/2003 | Boyer et al. | 623/23.6 |
| 6,706,067 B2* | 3/2004 | Shimp et al. | 623/17.11 |
| 6,719,794 B2* | 4/2004 | Gerber et al. | 623/17.11 |
| 6,855,167 B2* | 2/2005 | Shimp et al. | 623/17.11 |
| 6,902,578 B1* | 6/2005 | Anderson | A61B 2/28 623/16.11 |
| 6,986,788 B2* | 1/2006 | Paul et al. | 623/17.11 |
| 7,048,762 B1* | 5/2006 | Sander et al. | 623/17.11 |
| 7,048,765 B1* | 5/2006 | Grooms et al. | 623/17.16 |
| 7,087,082 B2* | 8/2006 | Paul et al. | 623/17.11 |
| 7,153,305 B2* | 12/2006 | Johnson et al. | 606/90 |
| 7,335,230 B2* | 2/2008 | Goulet et al. | 623/13.17 |
| 7,468,074 B2* | 12/2008 | Caborn et al. | 623/13.14 |
| 7,491,237 B2* | 2/2009 | Randall et al. | 623/17.11 |
| 7,648,509 B2 | 1/2010 | Stark | |
| 7,662,185 B2* | 2/2010 | Alfaro et al. | 623/17.16 |
| 7,726,002 B2* | 6/2010 | Shimp et al. | 29/525.01 |
| 7,763,072 B2* | 7/2010 | Bianchi et al. | 623/13.14 |
| D630,329 S* | 1/2011 | Goede et al. | D24/155 |
| 7,879,103 B2* | 2/2011 | Gertzman et al. | 623/17.16 |
| 7,938,857 B2* | 5/2011 | Garcia-Bengochea et al. | 623/17.11 |
| 8,007,533 B2* | 8/2011 | Zhukauskas et al. | 623/13.14 |
| 8,012,205 B2* | 9/2011 | Plouhar et al. | 623/13.17 |
| 8,291,572 B2 | 10/2012 | Grooms et al. | |
| 8,435,551 B2 | 5/2013 | Semler et al. | |
| 8,470,038 B2* | 6/2013 | Bianchi et al. | 623/13.14 |
| 8,579,975 B2* | 11/2013 | Myers | 623/13.14 |
| 8,617,241 B2* | 12/2013 | Myers | 623/13.14 |
| 8,961,606 B2* | 2/2015 | Laskowitz et al. | 623/17.16 |
| 2001/0016775 A1* | 8/2001 | Scarborough et al. | 623/17.16 |
| 2001/0032017 A1* | 10/2001 | Alfaro et al. | 623/17.11 |
| 2002/0016592 A1* | 2/2002 | Branch | A61B 17/1671 606/86 A |
| 2002/0016633 A1* | 2/2002 | Lin et al. | 623/17.11 |
| 2002/0029084 A1* | 3/2002 | Paul et al. | 623/23.63 |
| 2002/0038123 A1* | 3/2002 | Visotsky et al. | 606/73 |
| 2002/0138143 A1* | 9/2002 | Grooms et al. | 623/17.11 |
| 2002/0165611 A1* | 11/2002 | Enzerink et al. | 623/13.11 |
| 2003/0036800 A1* | 2/2003 | Meredith | 623/23.63 |
| 2003/0100948 A1* | 5/2003 | Goulet et al. | 623/13.17 |
| 2003/0105527 A1* | 6/2003 | Bresina | A61B 17/1637 623/17.16 |
| 2003/0139815 A1* | 7/2003 | Grooms et al. | 623/17.11 |
| 2003/0144743 A1* | 7/2003 | Edwards | A61L 27/3608 623/23.63 |
| 2003/0171811 A1* | 9/2003 | Steiner et al. | 623/17.11 |
| 2004/0249377 A1* | 12/2004 | Kaes et al. | 606/61 |
| 2005/0101957 A1* | 5/2005 | Buskirk et al. | 606/61 |
| 2005/0159812 A1* | 7/2005 | Dinger et al. | 623/13.14 |
| 2005/0229323 A1* | 10/2005 | Mills et al. | 8/94.11 |
| 2006/0052787 A1* | 3/2006 | Re et al. | 606/72 |
| 2006/0067971 A1* | 3/2006 | Story et al. | 424/426 |
| 2006/0178748 A1* | 8/2006 | Dinger et al. | 623/18.11 |
| 2006/0229730 A1* | 10/2006 | Railey et al. | 623/21.18 |
| 2006/0241760 A1* | 10/2006 | Randall et al. | 623/17.11 |
| 2006/0247790 A1* | 11/2006 | McKay | 623/23.44 |
| 2007/0185585 A1* | 8/2007 | Bracy et al. | 623/23.63 |
| 2007/0225805 A1* | 9/2007 | Schmieding | 623/13.14 |
| 2007/0276506 A1* | 11/2007 | Troxel | 623/23.63 |
| 2008/0188940 A1* | 8/2008 | Cohen et al. | 623/17.16 |
| 2008/0249622 A1* | 10/2008 | Gray | 623/17.11 |
| 2008/0269743 A1* | 10/2008 | McNamara et al. | 606/60 |
| 2009/0076551 A1* | 3/2009 | Petersen | A61F 2/4405 606/247 |
| 2009/0099661 A1* | 4/2009 | Bhattacharya et al. | 623/17.16 |
| 2009/0157119 A1* | 6/2009 | Hale | A61B 17/1659 606/247 |
| 2009/0216238 A1 | 8/2009 | Stark | |
| 2010/0106200 A1* | 4/2010 | Stark | 606/308 |
| 2010/0249930 A1* | 9/2010 | Myers | 623/13.14 |
| 2010/0249939 A1* | 9/2010 | Sluss et al. | 623/20.14 |
| 2012/0059469 A1* | 3/2012 | Myers et al. | 623/13.14 |
| 2012/0245703 A1* | 9/2012 | Meredith | A61F 2/28 623/23.51 |
| 2012/0271351 A1* | 10/2012 | Vestgaarden | A61B 17/1604 606/247 |
| 2013/0211523 A1* | 8/2013 | Southard et al. | 623/16.11 |
| 2014/0030309 A1* | 1/2014 | Yoo et al. | 424/423 |
| 2014/0121777 A1* | 5/2014 | Rosen et al. | 623/17.16 |
| 2015/0173902 A1* | 6/2015 | Southard et al. | 623/17.15 |
| 2015/0173904 A1* | 6/2015 | Stark | 623/17.15 |

OTHER PUBLICATIONS

Synthes GmbH, "Bone Graft Harvesting Set Technique Guide," © May 2010.

* cited by examiner

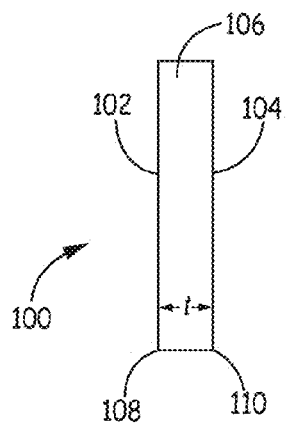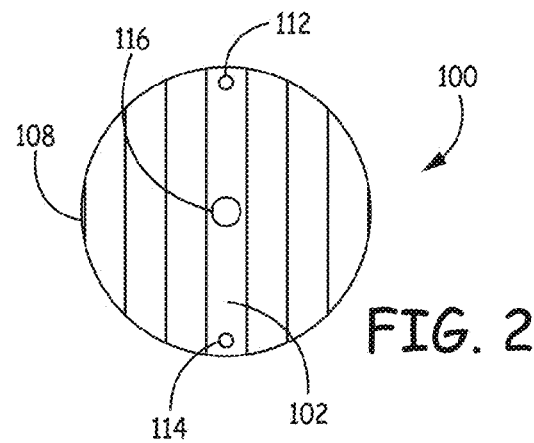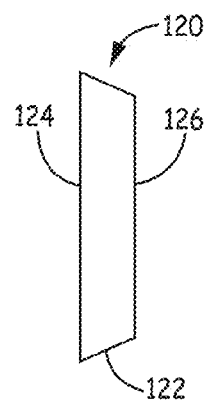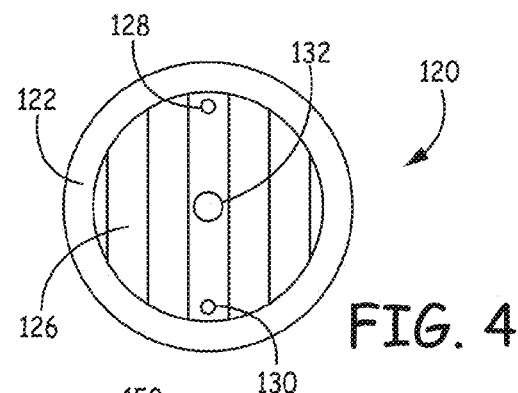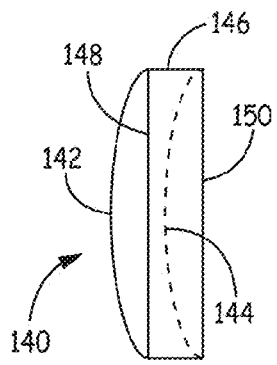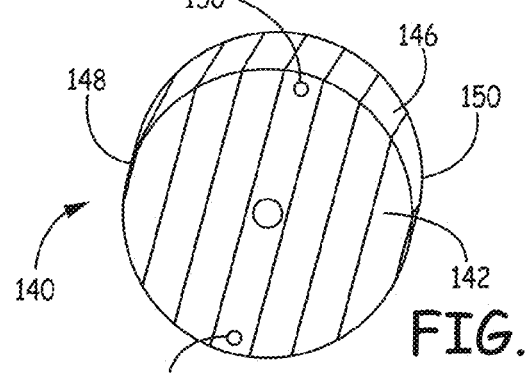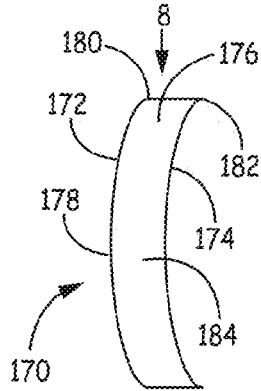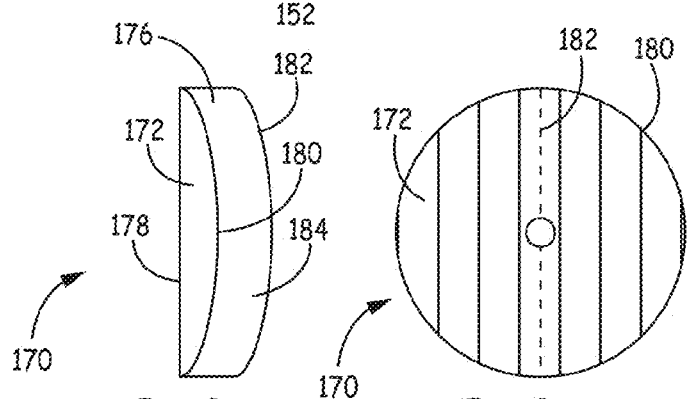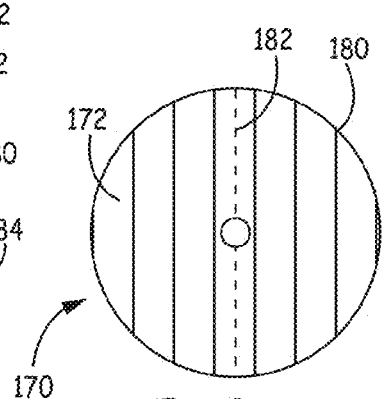

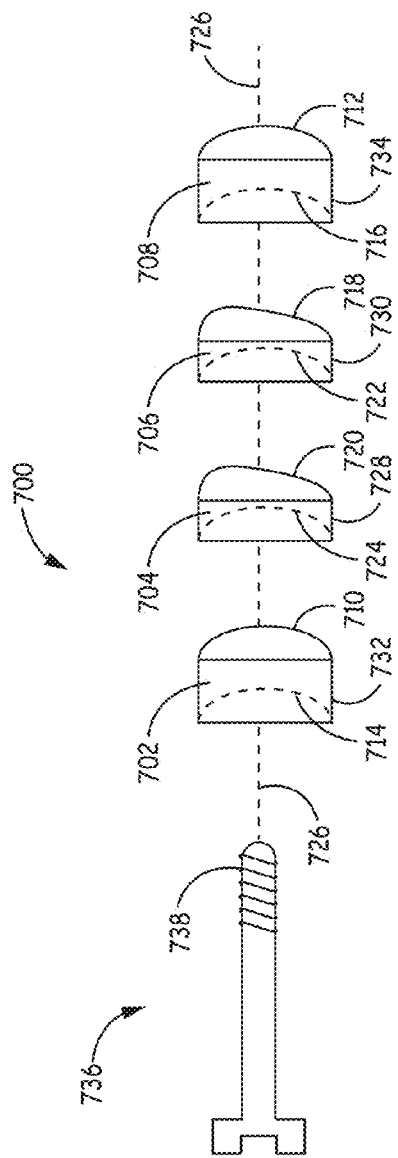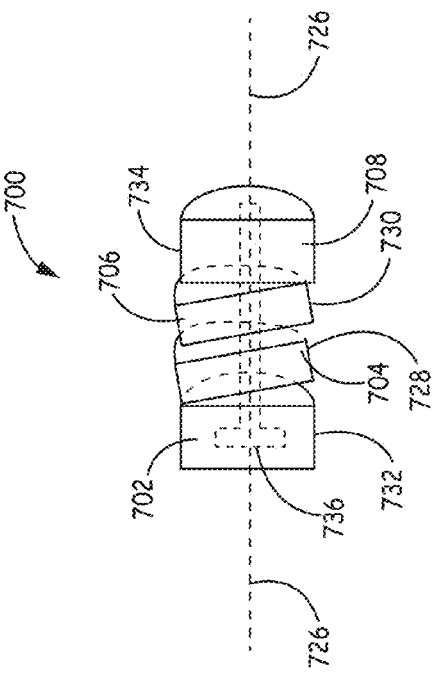

US 9,345,589 B2

BONE IMPLANTS FOR ORTHOPEDIC PROCEDURES AND CORRESPONDING METHODS

FIELD OF THE INVENTION

The invention relates to implants formed from harvested bone as well as to method for forming the implants and methods for inserting the implants.

BACKGROUND OF THE INVENTION

Various orthopedic procedures involve the placement of implants to modify the native skeletal structure within the patient. In particular, joint immobilization can involve the insertion of an implant with suitable placement to provide for target joint immobilization. In particular, spinal fusion is used to alleviate back pain in certain circumstances Immobilization of the sacroiliac joint can be used to alleviate pain associated with that joint. Implants can comprise various biocompatible metals to provide desired mechanical properties.

SUMMARY OF THE INVENTION

The a first aspect, the invention is directed to a bone implant element comprising cortical bone with any soft bone removed having a generally cylindrical longitudinal shape, a concave bottom surface and a visual indication of the lamellae orientation of the bone material.

In a second aspect, the invention is directed to a bone implant comprising a plurality of nested bone elements wherein the top surface of one element stably engages a bottom surface of another element with lamellae aligned within about 20 degrees.

In a third aspect, the invention is directed to a method for making a bone implant. The method comprises machining an inner surface of a generally cylindrical bone plug cut from the wall of a long bone to form a concave surface with cortical bone; and marking the orientation of lamellae in the bone.

In a fourth aspect, the invention is directed to a method for immobilizing a joint. The method comprises inserting a bone implant through a cannula having a generally cylindrical inner surface into a joint, the bone implant oriented with lamellae oriented within 20 degrees of an axis orthogonal to the surface bisecting the joint, wherein the bone implant has a longitudinal outer surface that is generally cylindrical with the bone implant being inserted with the generally cylindrical outer surface sliding within the cannula.

In a fifth aspect, the individual bone elements, may either before or after their insertion, be fixed to their bed, fixed to one another. Under fixation by a compressing or stabilizing screw, under the constraints of their geometry, they may shift into a roughly cylindrical implant with optionally sharp corners projecting outward from the cylinder

BRIEF DESCRIPTION OF THE DRAWINGS

FIG. 1 is side view of an embodiment of an implant element.

FIG. 2 is a top view of the implant element depicted in FIG. 1.

FIG. 3 is a side view of an alternative embodiment of an implant element having a tapered side surface.

FIG. 4 is a bottom view of the implant element depicted in FIG. 3.

FIG. 5 is a side view of a further alternative embodiment of an implant element having a concave lower surface and convex upper surface.

FIG. 6 is a top view of the implant element depicted in FIG. 5.

FIG. 7 is a side view of another alternative embodiment of an implant element that has top and bottom surfaces that are curved along one dimension and approximately uncurved in the orthogonal direction.

FIG. 8 is an orthogonal side view of the implant element depicted in FIG. 7.

FIG. 9 is a top view of the implant element depicted in FIG. 7.

FIG. 16A is an exploded side view of an embodiment of an implant having asymmetric elements and a screw to compress the elements.

FIG. 16B is a side view of the implant depicted in FIG. 16A, compressed with a screw.

DETAILED DESCRIPTION OF THE INVENTION

Figures 10A, 11, 12:
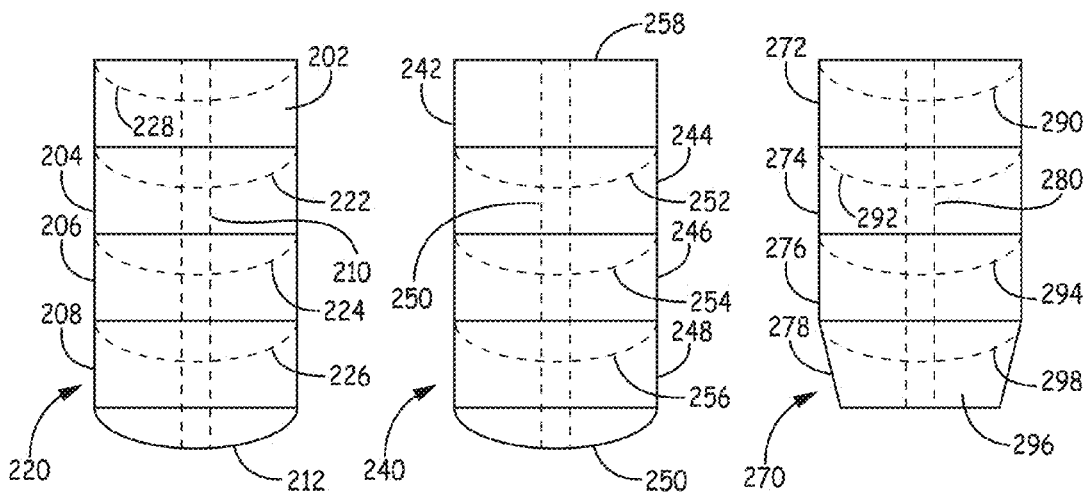
FIG. 10A is side view of an alternative embodiment of an implant having a stack of four implant elements with curved top and bottom surfaces.
FIG. 11 is a side view of another alternative embodiment of an implant having a stack of four implant elements with a bottom implant element with an approximately flat bottom surface and a curved top surface.
FIG. 12 is a side view of a further alternative embodiment of an implant having a stack of four implant elements with a top implant element with a tapered side surface.

Implants comprising cortical bone can be advantageously formed with some physical indicia indicating the orientation of the lamellae within the bone structure as well as in some embodiments a generally cylindrical symmetry for sides of the implant. Generally cylindrical side surface can provide for insertion into the joint through a cylindrical cannula or drill guide. In some embodiments, a set of bone interfacing bone segments can be useful as immobilization elements for insertion into a joint such that the interfacing bone implants can be used together to establish a desired dimension to the overall implant. The bone sections can comprise cortical bone selected for reasonably high strength. In some embodiments, the lamellae within the bone sections can be approximately aligned for placement across the joint and correspondingly the lamellae of adjacent matched bone segments can be appropriately aligned with each other. Aligned as just described, the strength and material properties of the original longitudinal orientation of lamellae in the bone sections can be maintained to provide higher strength along the greater stresses following implantation. Each bone section generally has a top, bottom and sides connecting the top and bottom surfaces. An average thickness generally can be specified as the average distance between the top and bottom surfaces. The top and bottom surfaces can be planar or contoured to interface with adjacent bone sections within the set. To facilitate placement and/or alignment of the sections within a joint, the bone sections can be cannulated, i.e., have a hole, generally through the thickness of the bone section. The cannulation provides for placement over a pin or the like during the implantation process. The outer surface of the bone sections can be convenient shapes for interfacing the joint. The bone sections can be conveniently designed for placement through a cannula within a suitably prepared joint space between bone surfaces. The use of multiple bone elements can be advantageously implanted to achieve desired implant size, and the multiple bone elements can be used without any joining of adjacent elements, adhesively joined adjacent elements or secured with a screw or the like.

The bone sections in particular can be conveniently adapted for sacroiliac joint immobilization that can be expected to lead to fixation of the joint. As used herein, the term "sacroiliac joint" refers to its intracapsular articular surfaces and the opposing surfaces of its adjacent recess (i.e. extra-articular region of the SI sacroiliac joint). Less invasive sacroiliac joint immobilization can be effectively adapted for insertion of the bone sections. Reference to the sacroiliac joint and positioning into the joint between the sacrum bone and the ilium bone includes the extra-articular recess as part of the joint and the space between the bones. The sacroiliac joint fixation procedures of particular interest do not generally pierce through both of the bones to compress them but involve placement into the joint following preparation to into the space between the bone thereby distracting the bone surfaces in contrast with procedures that go across the joint and compress the joint by pulling the bones together.

Various orthopedic procedures involve implantation of various prosthetic components to stabilize, repair or otherwise provide a desirable modification of the musculoskeletal system. While in principle, the set of interfacing bone sections can be used for various implantation purposes, the set of bone sections are particularly desirable for joint immobilization purposes since the combination of bone sections can provide a very strong material between the bone surfaces that can resist significant crushing forces. In general, metal implants can also conveniently provide desired mechanical properties for placement into a joint, or between the corresponding bone surfaces, for joint immobilization. However, bone can be used for patients with metal sensitivities that contraindicate metal use, and bone may provide better fusing over time for more stable joint fixation in some portion of the population. Also, the availability of useful bone-based immobilization elements can provide a desirable alternative material for physician selection during a procedure.

Bone sections generally can be formed from autograft, allograft or xenograft bone, and the patient can be a human, although the implants can be suitable for other mammals, such as mammalian farm animals. Bone tissue can be formed with an orientation to provide desired additional strength along stress lines. Thus, for example, bone in the legs has lamellae oriented along the rough axis of the bone such that the bone is particularly strong with respect to compressive forces and can support the weight of the person. This orientation of the bone can be advantageous in the use of the bone for a prosthetic implant. As described further below, the bone can be harvested with the orientation noted so that the processed bone sections have a known orientation relative to the stronger orientation of the original whole bone. In some embodiments, the lamellae can be approximately aligned in the set of bone sections. For example, marks can be noted on the bone prior to cutting a section of bone from a leg bone, and the marking can be preserved or reinforced as the bone is processed. Processing generally can involve removing weaker inner bone, contouring the bone fragments for alignment purposes and/or texturing the sides of the section. If the lamellae are approximately aligned in the set of bone sections, the implant can be correspondingly inserted in an aligned orientation upon placement into a patient, such as within a joint, such that the compressive forces in the joint or other location are aligned against the strong axis of the bone section to resist crushing of the properly oriented bone section.

While individual bone sections can be effectively implanted into a patient, it can be desirable to use a set of interfacing bone sections to provide desired stabilization of a joint or other implanted position. For example, it can be desirable to use two, three or more bone sections. The top of one bone section interfaces with a bottom of an adjacent section. While the top and bottom surfaces can be generally flat, with or without texturing, to interface with each other, it can be desirable to have curved surface that interface to provide additional facilitation of alignment of the set of sections. For example, the surfaces can be roughly spherical (generally with a radius of curvature significantly greater than the linear dimensions of the implant) or in some embodiments, approximately curved along one axis. The curve along one dimension may or may not be approximately cylindrical. The advantage of a curve in one dimension is that shape can be more reminiscent of the original harvested bone's shape so that a greater fraction of the bone mass can be used in forming the bone section and the orientation of the lamellae can be clear from the shape of the structure without the addition of a separate visual marker.

The shape formed by the edges of the elements can in principle be machined to have various desired shapes. However, a generally cylindrical shape provides for insertion into a cylindrically shaped drilled channel, and may also use of a greater fraction of the harvested bone if the bone fragment is harvested from the bone as a cylindrical element. As described further below, the bone is generally drilled out conveniently during harvesting from the bone in a cylindrical shape. Thus, in some embodiments, the initial cylindrical shape can be substantially maintained, although tapering, rounding, smoothing, texturing, threading or notching may be desirable. The elements may also be provided with a central hole, generally relatively small as described further below, to provide to placement into the patient over a pin or other tool to facilitate placement in a less invasive procedure. The central hole may be used for the placement of an intra-elemental or compressing screw. If the hole is small, the hole may not negatively affect the mechanical strength significantly.

In some embodiments, the bone implants may be processed to facilitate incorporation. In some embodiments, the implant or implant element can be machined to have a textured a side surface. The texture can include, but is not limited to, divots, craters, and/or corrugations. The textured side surface can promote adherence between the implant and a prepared bed within the joint when the implant is inserted into the joint. In such embodiments, the improved grip can help to prevent rotation and/or translation of the implant within the joint. In implant embodiments comprising a plurality of implant elements, the top and/or bottom surfaces of the implant elements or selected portions thereof can be textured. In such embodiments, texturing can promote adherence between the implant elements. In some embodiments, the implant can be chemically treated to decalcify or remove antibodies therefrom. Suitable acids include any non-toxic acid at an appropriate pH, such as hydrochloric acid of appropriate purity and concentration. In some embodiments, the implants can be coated with a composition to facilitate bone growth onto the implant. Suitable coating compositions include, but are not limited to, hydroxyapatite. Surface texturing can be effective to facilitate incorporation, or ongrowth of healing processes.

Cortical bone implants for specific spine procedures with a "D" or "bread-load" shaped implants are described further in U.S. Pat. No. 8,291,572 to Grooms et al., entitled "Multi-Component Cortical Bone Assembled Implant," incorporated herein by references. The shape and orientations of the implants can differ significantly from embodiments of the implants described herein. The use of bone based implants for sacroiliac fixation are described generally in U.S. Pat. No. 7,648,509 to Stark, entitled "Sacroiliac Joint Immobilization," and published U.S. patent application 2010/0106200 to Stark, entitled "Bone Screws and Particular Applications to Sacroiliac Joint Fusion," both of which are incorporated herein by reference. However, these applications of bone implants do not describe any particular features of the bone implant structure. The orientations and shapes of the bone implants described herein can be conveniently used in particular for joint immobilization using a cylindrical cannula/drill guide for placement of the implants in an orientation to take advantage of the greater strength along the preserved alignment of the lamellae of the original whole bone.

A set of implants can be designed for placement into a joint with the sides of the implant supporting the forces of the joint. The lamellae of the bone can be particularly oriented across the joint to support the forces of the joint to reduce the crushing of the implant. The generally cylindrical shape of the sides of the implant provide for insertion through a cylindrical cannula/drill guide with some tapping or gentile pounding to place the implant into the prepared area, such as following drilling.

The bone sections can be particularly effective for sacroiliac joint immobilization. In particular, fixation of the sacroiliac joint can be effective for the alleviation of buttock and lower back pain in individuals in which other treatments may be ineffective. Tools have been developed for the efficient and effective less invasive approach for sacroiliac joint immobilization, which is described in published U.S. patent application 2009/0216238 (the '238 application) to Stark, entitled "Tools For Performing Less Invasive Orthopedic Joint Procedures," incorporated herein by reference. The set of bone sections can be sized for delivery through the cannula and over the pin for guided placement into the sacroiliac joint.

The bone implants described herein provide an alternative to metal implants to provide options to health care professionals performing joint immobilization procedures. For example, the bone implants can be used for patients with sensitivity to metal implants, and the bone implants may provide improved fusion of the joint in patients with reduced bone healing potential. Thus, it is believed that the bone implants provide a desirable choice for procedures complementary to implants as described in published U.S. application 2010/0106200 to Stark, entitled "Bone Screws and Particular Applications to Sacroiliac Joint Fusion," incorporated herein by reference. The improved bone implants described herein can provide improved strength across the joint between opposing bones to reduce the chance of fracture of the bone implants. While desirable embodiments of the bone implants can be implanted into a patient without metal support structures, in some alternative embodiments a screw or other support elements can be included if desired to further supplement the bone elements.

Implants

The improved bone implants described herein generally have indicia that provide for orientation of the strong dimension of implant, along lamellae, across the joint such that the implant is not crushed by forces within the joint, or between bone surfaces. The orientation of the lamellae can be provided by a physical marking or in some embodiments by the shape of the implant. While it may be desirable to use implants with various shapes of the implant sides, generally cylindrically symmetric implants can be effectively delivered through a cylindrical cannula or drill guide into a cylindrically drilled channel. Indicia can be placed on the implant element to indicate the general orientation of lamellae within the bond structure indicating a strong orientation of the element. An implant with cylindrically symmetric side surfaces can be tapered or cylindrical. The top and bottom surfaces can be planar or curved in two dimensions (e.g. a bent disc) or curved in three dimensions (e.g. a dome). For use in a stack, the bottom surface of one implant can be contoured to interface with good contact with the top surface of another element so that a set of elements can be used essentially as components of the implant formed from the set. A hole through the elements can be useful for the delivery of the element over a pin and/or to facilitate alignment and/or delivery of the implant.

Referring to FIGS. 1 and 2, a representative embodiment of an implant element 100 is shown with a top surface 102, bottom surface 104, and side surface 106. Generally, designation of a top surface and bottom surface are essentially arbitrary and can be reversed. A top edge 108 separate top surface 108 from side surface 106, and a bottom edge 110 separates bottom surface 104 from side surface 106. Edges 108, 110 may or may not be sharp but are nevertheless readily identifiable as edges. Indicia 112, 114 are aligned to indicate the approximate orientation of the lamellae of the bone, such as along the line formed by indicia 112, 114 although other known relationships can be used as desired. Indicia 112, 114 can be formed using a visual indicator, such as a colored paint or dye, and/or a marker that can be felt, such as a bump, divot, roughness or the like. The average thickness of the implant is the average distance from top surface 102 to bottom surface 104, and the thickness is denoted "t" in FIG. 1. In some embodiments, the side surface has approximate cylindrical symmetry around an axis through the implant, such as cylindrical symmetry shown in FIG. 2. A central hole 116 can be used to engage element 100 on a pin or the like.

Referring to FIGS. 3 and 4, implant element 120 has circular cross sections with tapered side surface 122. FIG. 3 is a side view, and FIG. 4 is a bottom view. As seen in FIG. 4, implant element 120 has cylindrical side surfaces 122 and flat top surface 124 and flat bottom surface 126. Top surface 124 has a greater area than bottom surface 126. Referring to FIG. 4, indicia 128, 130 are used to provide information on the orientation of the lamellae. As shown in FIG. 4, indicia 128, 130 are provided on the bottom surface of implant element 120, but additionally or alternatively, indicia can be placed on the top surface. Hole 132 pass through roughly the center of top surface 124 and bottom surface 126. In a stack of elements, a tapered element can be a lead element of the stack in some embodiments. In additional or alternative embodiments, the top surface and/or bottom surface can be curved to interface with an adjacent element which may or may not have tapered edges, such as the embodiments in FIGS. 5-9.

Generally, the average thickness of an implant element can be from about 2 millimeters (mm) to about 15 mm, in further embodiments from about 2.5 mm to about 12 mm, and in other embodiments from about 3 mm to about 10 mm. For cylindrical implant elements for some applications, the radius can be from about 4 mm to about 20 mm, in further embodiments from about 5 mm to about 18 mm, and in additional embodiments from about 6 mm to about 15 mm. Hole size to allow passage over a guide pin can be from about 2 mm to about 5 mm and in further embodiments from about 2.4 mm to about 3.5 mm. Generally, the area of the top surface and/or bottom surface of an implant element can be from about 30 $mm^2$ to about 1200 $mm^2$, in further embodiments from about 40 $mm^2$ to about 750 $mm^2$, and in additional embodiment from about 50 $mm^2$ to about 600 $mm^2$. A person of ordinary skill in the art will recognize that additional ranges of implant element dimensions within the explicit rages above are contemplated and are within the present disclosure. The surface area is increased or decreased by the geometric or chemical modifications to introduce structural elements along the surface, texture, porosity or the like through machining, material deposition, or chemical etching/pitting of the surface.

Curves surfaces for the elements can provide for a convenient interface of adjacent elements when a plurality of elements is combined for an implant. In general, a plurality of elements is combined for use to provide desired dimensions for the implant, as described further below. FIG. 5 shows a side view of an implant with a concave lower surface and a convex upper surface. The upper and lower surfaces are approximately matched so that two equivalent elements can nest well in a stable configuration adjacent each other as elements of an implant comprising a plurality of such elements. The surfaces can be portions of a spherical shaped surface or other suitable geometric shapes. Referring to FIG. 5, implant 140 has curved top surface 142 and curved bottom surface 144 (shown with a phantom line) connected by side surface 146 at edges 148, 150. Top surface 142 is shown in FIG. 6 with the orientation of lamellae displayed as roughly straight lines along the curved surface, although the lamellae may not actually be visible in the bone. Indicia 150, 152 are placed to orient the lamellae visually.

As shown in FIG. 5, side surface has small ridges extending approximately linearly between top surface 142 and bottom surface 144. Various other patterning and/or texture can be placed along side surface 146 as well as other embodiments of the implant element including but not limited to side surfaces 106 and 122. Patterning and/or texture can increase the surface area of the side surfaces, top surface and/or bottom surface, or portions thereof of an implant element and improve adherence between an implant element and adjacent bone following implantation. In some embodiments, the top and bottom surfaces of implant elements can be patterned and/or texture to improve adherence between individual implant elements in a stacked configuration. If desired, texture on the top and/or bottom surfaces of an implant element can inhibit shifting of adjacent elements relative to each other in a stacked orientation. Other suitable patterning can include, for example, small bumps, craters, or divots; horizontal ridges; and the like and suitable texturing can include, for example, surface roughness. Coating of the implant, such as with hydroxyapatite can also introduce texturing. Based upon the teachings herein, patterning and/or texturing can be engineered using mechanical and/or chemical processing techniques well known in the art.

As noted above, in some embodiments, the surfaces of the implant element can be curved along 1 dimension and approximately flat along the orthogonal direction. In some embodiments, the surfaces can be approximately portions of a cylinder such that the curve is approximately a portion of a circle, although other reasonable curved shapes can be used as desired. Referring to FIG. 7, a side view of implant 170 viewed along the curved orientation of the implant with top surface 172, bottom surface 174 and side surface 176. Top surface 172 has a ridge 178. The orthogonal side view is shown in FIG. 8, with the direction of the view relative to FIG. 7 indicted by arrow 8 in FIG. 7. In the view of FIG. 8, the curvature is visible along two edges 180, 182 separated by side surface 184, and top surface 172 is visible due to the curvature extending the top surface out relative to the line of edge 180. FIG. 9 shows a top view in the general orientation of FIG. 8. Dashed line 182 indicates roughly the plane of the axis around which the curvature is made. Hole 184 is located approximately at the center of top surface 172 and extends through element 170. Due to the planar symmetry along line 182, the orientation of the lamellae can be oriented by the shape of the element. As shown in FIG. 9, the orientation of the lamellae are shown with lines roughly parallel to line 182, although the element can be machined to have different orientations at the possible expense of less usage of bone due to the natural shape of bones. While separate indicia can be used to visualize the orientation of the lamellae, the shape can be a convenient indicator alone. Other variations are possible such as a saddle shape, e.g., a hyperbolic paraboloid, with opposite curvatures in orthogonal directions, which can provide additional nesting stability. Similarly, an element can be a hybrid of the elements in FIGS. 1-2 and either the elements of FIG. 5-6 or 7-9, in other words, a top surface can be flat while the bottom surface is curved in either 1 or two dimensions. A flat top surface may be desirable to engage a chisel or other tool used to drive the implant into place while the bottom surface is curved to desirably engage an adjacent element.

In some embodiments, a stack of implant elements are used to provide an overall implant dimension desired for a particular use. The number of implants can be selected based on the overall implant size, in particular length, desired in view of the dimensions of the individual elements. In some embodiments, 2, 3, 4, 5, 6 or more implant elements can be used together in a single implant. Thus, an implant can have in some embodiments an overall length for placement into an adult human sacroiliac joint from about 10 millimeters (mm) to about 45 mm, and in further embodiments, from about 15 mm to about 35 mm. For use in other joints, the implant generally can have a length from about 10 mm to about 80 mm. Also, an implant can have a diameter for insertion into an adult human sacroiliac (SI) joint from about 6 mm to about 28 mm and in other embodiments from about 8 mm to about 25 mm. A person or ordinary skill in the art will recognize that additional ranges of implant dimensions within the explicit ranges above are contemplated and are within the present disclosure. Each element of the implant can be equivalent to other elements of the implant, or in other embodiments some implant elements can be distinct from others. In some embodiments, the initial element and/or the final element can be distinct. For example, the initial element can have tapered edges to facilitate insertion, and/or the final element can have a flat top surface to engage a driving element.

Implant elements forming the implant can be either attached or free floating. While anticipating tight element stacking and tight packing between bone surfaces, the elements and implants can have shapes and sizes to allow for motion, bone quality, ease of approximation, collapse, or subsidence. In other construct embodiments, the implants can be affixed to one another mechanically, by screw or similar fastener, or by adhesive, or geometry.

To obtain desired strength along the length of the stacked implant, it can be desirable to orient the lamellae of the individual elements in approximate alignment. In particular, it can be desirable to orient the lamellae of one element within about 20 degrees of an adjacent element, in further embodiments within about 15 degrees and in additional embodiments within about 10 degrees of each other. It is possible for the elements to be aligned with the adjacent lamellae oriented within no more than about 5 degrees of lamella orientation in an adjacent element. A person or ordinary skill in the art will recognize that additional ranges of orientation alignment within the explicit ranges above are contemplated and are within the present disclosure.

FIG. 10A shows a stack of implant elements forming an implant. Referring to FIG. 10A, implant 200 comprises elements 202, 204, 206, 208. As shown in FIG. 10A, each element has curved top and bottom surfaces as with element 140 of FIGS. 5 and 6. An optional channel 210 formed by holes through the center of each element is shown in phantom lines in FIG. 10A. Bottom surface 212 of element 208 is visible. Curved interfaces 222, 224, 226 between adjacent top and bottoms surfaces of adjacent elements are shown in phantom lines, and a curved top surface 228 of element 202 is shown in phantom lines in FIG. 10A. The adjacent implants can be held together by placement. In additional or alternative embodiments, the adjacent elements of the implant can be held together with a fastening element, such as a clip, screw, bolt or the like. Furthermore, a biocompatible adhesive can be used to adhere elements together in the implant, and suitable adhesives can include, for example, surgical glues, as described further below. A screw or attachment device may hold the bone implants in proximity by compressing them to the bone bed.

Figures 13, 15A:
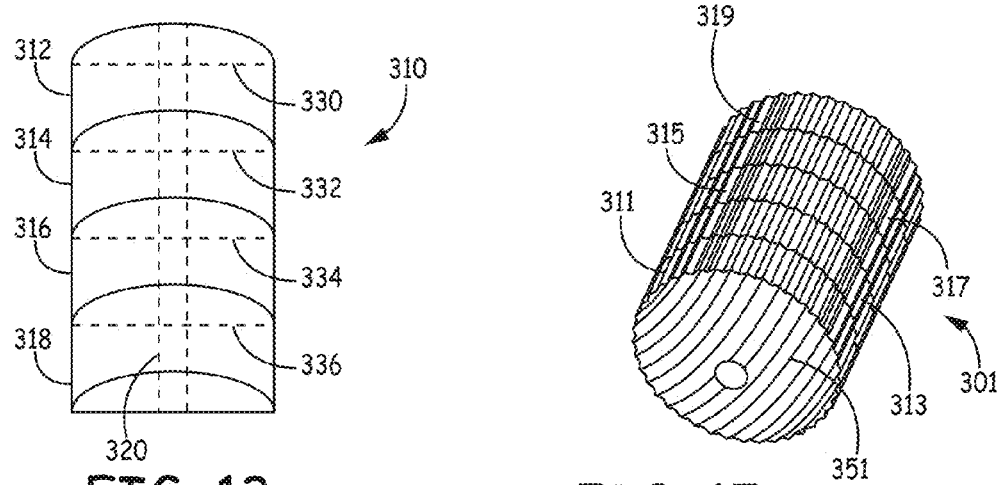
FIG. 13 is a side view of an additional alternative embodiment of an implant having a stack of four implant elements that are curved along one dimension and approximately flat in the orthogonal direction.
FIG. 15A is a perspective view of a specific embodiment of an implant having implant elements with indicia indicating the orientation of the lamellae on the side surfaces.
Figure 14:
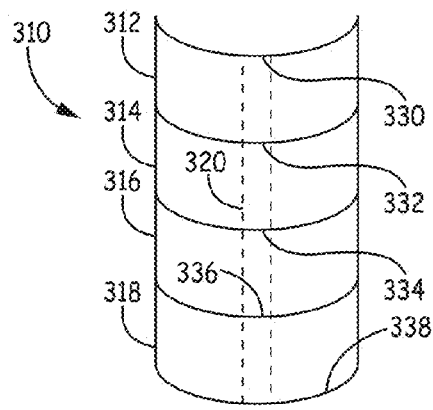
FIG. 14 is an opposite side view of the implant depicted in FIG. 13.
Figure 10B:
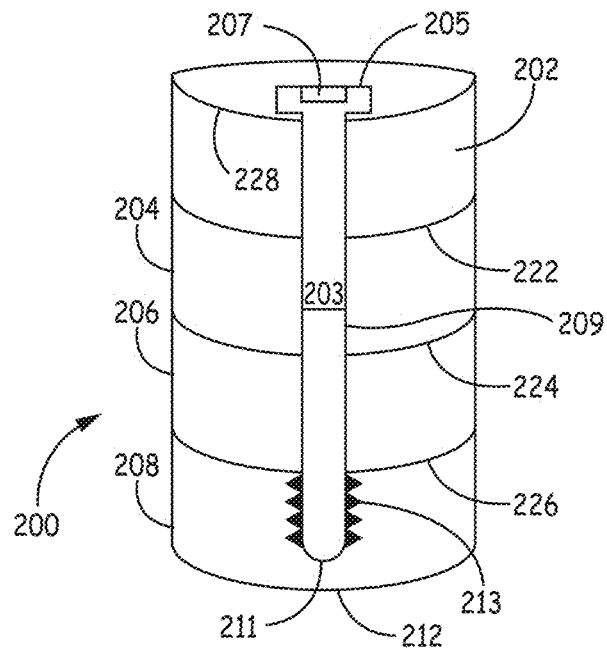
FIG. 10B is a cross section of the implant depicted in FIG. 10A, secured with a screw.
Figure 10C:
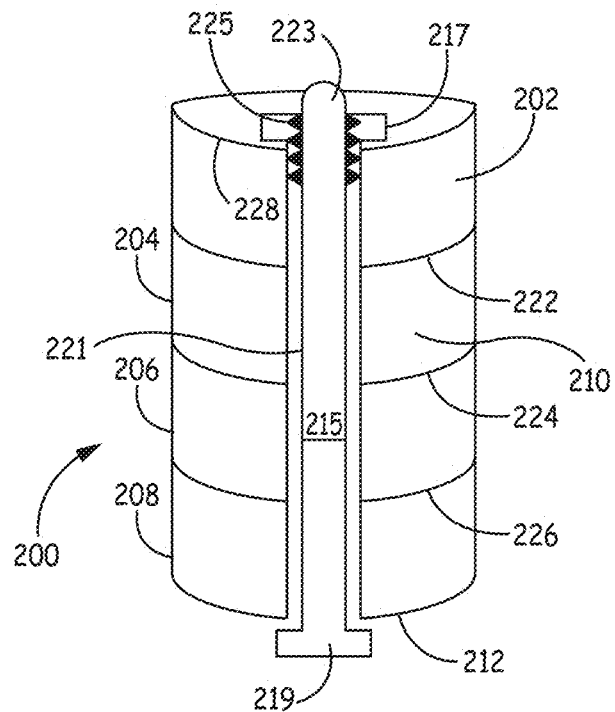
FIG. 10C is a cross section of the implant depicted in FIG. 10A, secured with a bolt and nut.

Elements of the implant may have asymmetries that adjacent elements do not rest against each other with closely matched surfaces, and the addition of longitudinal forces can draw the elements together based on the respective shapes that provide translational forces. The movement of the elements relative to one another can be designed to provide gripping of the bone adjacent the implant to hold the implant more securely. FIGS. 10B and 10C show implant 200 secured together with a screw and bolt, respectively. The screw initially can be inserted without tension such that the elements are held as a unit without drawing the elements significantly together. Referring to FIG. 10B, elements 202, 204, 206, 208 are secured with screw 203. Screw 203 comprises head 205, comprising engagement element 207, at one end of shaft 209 and tip 211, comprising threads 213, at the other end of shaft 209. Engagement element 207 is configured to interface with a driver to drive screw 203 through the implant elements. The length of shaft 209 is generally selected so that tip 211 does not extend significantly past the bottom surface of element 208 when head 205 is seated against top surface 227 of element 202 as long as at least some threads have purchase in element 208. In some embodiments, tip 211 can comprise a cutting flute. In some embodiments, threads 213 can extend along shaft 203 from tip 211 to head 205. Referring to FIG. 10C, elements 202, 204, 206, 208 are secured with bolt 215 and nut 217. Bolt 215 comprises head 219 at one end of shaft 221 and tip 223, comprising threads 225, at the other end of shaft 221. The length of shaft 209 is selected so that threads 225 engage bolt 217 when head 219 is seated against bottom surface 212 of element 208. In some embodiments, threads 213 can extend along shaft 221 from tip 223 to head 219. Based on the teachings herein on formation of the elements, the implant design can take corresponding ranges of designs. Some representative variations are shown in FIGS. 11-13. Referring to FIG. 11, implant 240 comprises elements 242, 244, 246, 248 forming an optional channel 250 when aligned. Bottom surface 250 of element 248 is visible, and interfaces 252, 254, 256 are shown in phantom lines between adjacent elements. Elements 244, 246, 248 are analogous to elements 204, 206, 208 of implant 200. Element 242 has a flat top surface 258 in contrast with the curved surface of element 202 of FIG. 10. Referring to FIG. 12, implant 270 comprises elements 272, 274, 276, 278 forming an optional channel 280 when aligned. Elements 272, 274, 276 are similar to elements 202, 204, 206 of implant 200, and elements 272, 274, 276 have a curved top surface 290 and curved interfaces 292, 294. Element 278 has tapered side surface 296 similar to element 120 of FIGS. 3 and 4, although element 278 has a concave top surface forming curved interface 298 with element 276, unlike the flat surface of element 120. FIGS. 13 and 14 shows alternative side views of an implant 310 formed form a stack of elements similar to those shown in FIGS. 7-9. Implant 310 comprises elements 312, 314, 316, 318 which align to form optional channel 320. Due to the curvature along one axis, the curvature is visible directly in the view of FIG. 14, which is analogous to the view of FIG. 7. In the orthogonal view of FIG. 13, straight edges are visible corresponding to the non-curved orientation of the elements with phantom lines showing the ridges 330, 332, 334, 336 formed by the curved surfaces at the center of the curves as shown in FIG. 14. The bottom surface of element 318 has curved surface 338 terminating at edge 338.

Figure 15B:
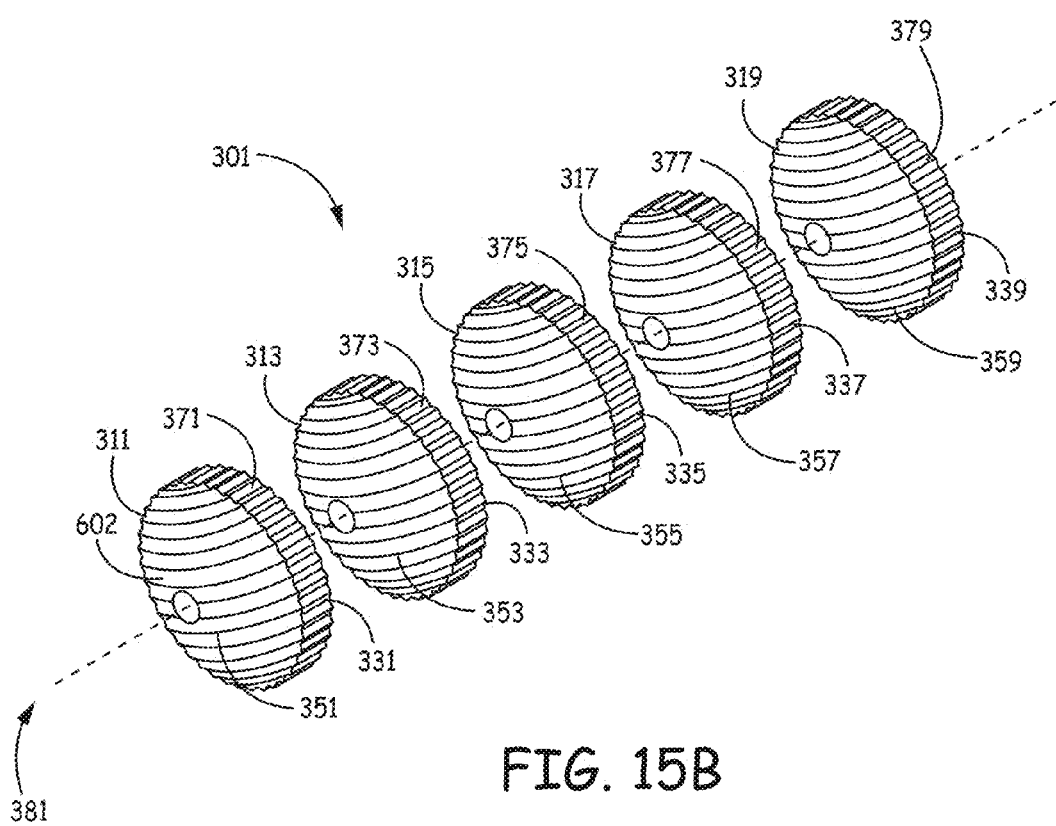
FIG. 15B is an exploded, perspective view the implant depicted in FIG. 15A.

FIGS. 15A and 15B show a perspective view of a particular implant embodiment. Referring to the figures, implant 301 comprises implant elements 311, 313, 315, 317, 319. As seen better in the exploded view of FIG. 15B, the bottom surfaces of the each element is convex, and the top surfaces are concave to match the adjacent bottom surfaces, which follows from the view in FIG. 15A even though the top surfaces are not explicitly shown. Thus, the top and bottom surfaces are analogous to the respective surfaces shown for the implant elements in FIG. 10A. Implants elements 311, 313, 315, 317, 319 have respective indicia 331, 333, 335, 337, 339 that indicate the alignment of lamellae in each corresponding implant element. The orientation of the lamellae in implant elements 311, 313, 315, 317, 319 is represented by lines 351, 353, 355, 357, 359, respectively (for clarity, only representative lines are numbered). Implant elements 311, 313, 315, 317, 319 have textured side surfaces 371, 373, 375, 377, 379 comprising ridges. The textured sides surfaces may increase frictional forces between the joint and the implant elements to help guard against undesirable movement of implant elements 311, 313, 315, 317, 319 within the joint. Implant elements 311, 313, 315, 317, 319 have holes that form a channel 381 extending through implant 301 when placed in a stacked configuration, as shown in FIG. 15B.

In some embodiments, an implant can comprise elements with engineered surface geometries that translate under the effects of a compressing force in a predictable way. In such embodiments, the edges of the shifted elements, can react under the forces of compression with respect to one another, altering the external surface of the composite implant so that the side surface of the shifted elements become non-cylindrical. The edges extending from the non-cylindrical surfaces within a joint can provide for added distraction anti-rotation and/or anti-migration properties of the implant. In particular, when the composite implant is compressed and in the joint, the edges of the shifted side surfaces can increase the outward hoop stresses on the bones of the joint and can provide for improved fixation of the implant. The implant elements can be compressed before or after insertion into the joint. A screw, a bolt or the like inserted into the implant elements can provide for compression of the implant elements.

In some embodiments, implant elements engineered with asymmetric bottom surfaces can shift under compression. Correspondingly, when compressed in a stack, the interface between the asymmetric bottom surface of one element and the symmetric top surfaces of adjacent elements cause the elements to shift out of alignment such that the side surfaces of the elements become un-aligned when the implant elements are compressed. FIGS. 16A and 16B show side views of an implant having elements with asymmetric bottom surfaces that shift when compressed. Referring to FIGS. 16A and 16B, implant 700 comprises symmetric elements 702, 708 and asymmetric elements 704, 706. Symmetric elements 702, 708 have symmetric, convex bottom surfaces 710, 712 and symmetric, concave upper surfaces 714, 716. Asymmetric elements 704, 706 have convex bottom surfaces 718 and 720. Asymmetric element 706 has a symmetric, concave upper surface 722 and asymmetric element 704 has an asymmetric, concave upper surface 724. In other embodiments, asymmetric element 704 can have a symmetric, concave upper surface. When elements 702, 704, 706, 708 are compressed along reference line 726, the interface between the asymmetric bottom surfaces of elements 704 and 706 and respective symmetric upper surfaces of elements 706 and 708 cause elements 704, 706 to shift relative to reference line 726. The shift in elements 706, 708 when implant 700 is compressed is depicted in FIG. 16B. As seen in FIG. 16B side surfaces 728, 730 of elements 704,706 are not aligned with side surfaces 732,734 or elements 702,708. Screw 736, comprising a tip with threads 738 is driven through the implant to compress elements 702, 704, 706, 708.

Processing to Form Implants

The implants can be formed from portions of allograft, autograft or xenograft bone. The bone is processed under conditions in which the living tissue is no longer viable so that the mineral bone structure remains. In general, bone plugs are harvested from areas of cortical bone on a donor bone and processed into implant elements. Cortical bone is the stronger, more dense outer portion of the bone. In some embodiments, following extraction, indicia indicating the alignment of lamella within the bone plug are added to the bone plug. The harvested bone plug can be processed to provide implant segments with a variety of selected geometries according to the designs described above. In some embodiments, implant segments can be formed into stacked configuration at and/or prior to insertion into a patient.

In general, any allograft, autograft or xenograft bone having a desirable amount of cortical bone may be used for harvesting bone plugs. In some embodiments, however, the use of long bones as donor bones in combination with selected harvesting approaches may have particular processing advantages due to the size of the bones. Long bones can be a significant source of cortical bone and generally comprise an outer portion comprising cortical bone and an inner portion comprising cancelleous bone and a medullary canal. The mineral formed into the bone structure is oriented generally along stress lines, and lamellae can organize the mineralization along collagen sheets to improve the strength of the bone. Long bones of the body are organized into a lamellae structure that resist the typical life and activity stresses of the living individual. The lamellae of the cortical bone are generally aligned along the long axis of the long bone diaphysis. Bone segments harvested generally perpendicularly to the long axis of the bone thus can comprise cortical bone with lamella aligned in a specific orientation generally parallel to the top and bottom surfaces of the extracted bone portion. The as-harvested structure of the resulting bone plugs correspondingly have a known lamellae orientation across the bone plug and, therefore, can allow for convenient placement of indicia indicating the orientation. Suitable long bones include, but are not limited to, the femur, humerus and tibia.

Figure 17:
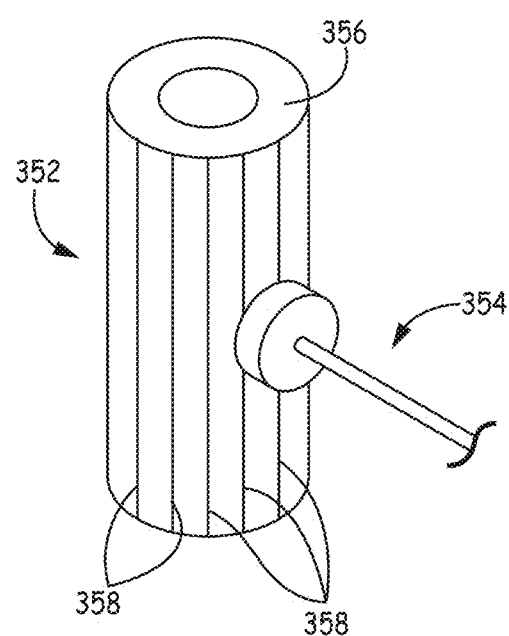
FIG. 17 is a schematic depiction showing the orientation of a cutter in relation to a donor bone in one embodiment of a bone plug harvesting procedure.
Figure 18:
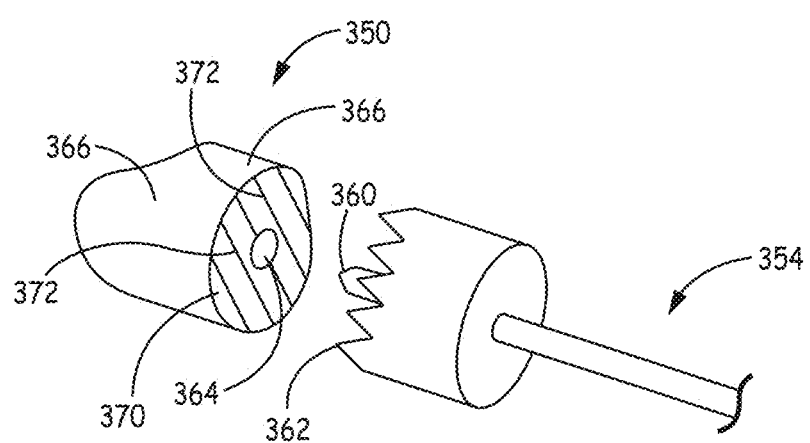
FIG. 18 is a perspective view of a bone plug harvested from a donor bone in relation to a cutter.
Figure 19:
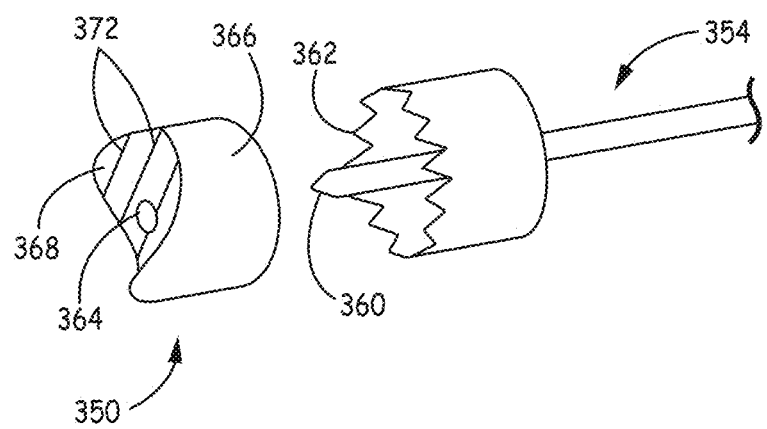
FIG. 19 is a different perspective view of the bone plug and cutter depicted in FIG. 18.

FIGS. 17-19 show schematic depictions of one embodiment of a bone plug harvesting process. Referring to the figures, bone plug 350 is harvested from bone 352 using cutter 354. Bone 352 is represented by a cylindrical shell, with outer wall 356 representing a region of cortical bone. For hard bones of interest, bone 352 has an approximately known lamellae orientation based upon the type of bone and the orientation along the shape of the bone, as indicated by lines 358. In general, to harvest a bone plug, cutter 354 is aligned to drill generally perpendicularly to an axis of the bone, with the lamellae generally oriented also roughly along the length. Bone plug 356 is harvested by drilling into bone 356. The end of cutter 354 comprises central drill tip 360 and cutting teeth 362. During harvesting, central drill tip 360 can form a channel 364 through harvested bone plug 350. In some embodiments, the diameter of drill tip 360 can be selected such that channel 364 is sized to fit over an implant insertion pin. Additionally or alternatively, channel 364 can be created and/or re-sized during post-processing as described below. In alternate embodiments, the orientation of the lamellae relative to the implant element may be engineered by machining away of bone from partial sections of bone or bone fragments. Novel shapes, with novel strength orientations, for specific applications may be obtained either by cutting the bone out of a segment, or shaping it from a segment by machining, rather than cutting it from a whole section of bone. Other cutting/machining techniques can be used as desired to harvest the element from the bone.

Following extraction, it can be desirable to note or maintain the orientation of bone plug 350 relative to bone 352 so that indicia, as described above, can relatively easily be added to harvested bone plug 350. In general, the lamellae of harvested bone plug 350 are not discernable by visual inspection. For the embodiment shown in FIGS. 17-19, the orientation of the lamellae can be roughly ascertained from the curvature of the surfaces, at least prior to further processing. Correspondingly, by noting and/or maintaining the orientation of bone plug 350 relative to bone 352 after harvesting, indicia indicating the alignment of lamella can be readily added to bone plug 350. Indicia can include a visual indicator, such as a colored paint or dye, and/or a marker that can be felt, such as a bump, divot, roughness or the like and/or a notched drill channel. In some embodiments, if desired indicia is desirably added by machining the bone plug (e.g. roughness or a notched drill channel), a first indicia such as a visual indicator can be added first. The bone plug can then be taken to an appropriate tool station to add the machined indicia using the first indicia as a reference. For stacked implant elements, it can be desirable to add indicia in the same manner for each implant element so that when the indicia of each implant element are aligned, the lamellae of each implant element are aligned.

In general, indicia can be placed on bone plug 350 at a location(s) that it is (are) visible to the physician prior to and/or after the ultimately formed implant is delivered into a joint. For example, the sides of the implant are generally visible prior to insertion of the implant into the joint and indicia can be placed on side surfaces, for example, as indicated in FIG. 16. In a cannulated insertion procedures, as described below, the sides of the implant are generally not visible to the physician after the implant is placed within the cannula. In some embodiments, it can be desirable to have indicia that are visible on a top surface and/or bottom surface of an implant element as an alternative or in addition to indicia along a side surface. Regardless of the insertion procedure, in some embodiments, indicia placed on a top surface or bottom surface of an implant can be desirable because it can allow a physician to confirm that the lamellae are desirably aligned after the implant is inserted into the joint and to determine whether revision is desired.

The extracted bone plug can be processed to form selected features as described above. Generally, processing can comprise shaping the top, bottom and/or side surfaces of a bone plug to obtain the desired implant element shape and/or size as well as to remove any bone of less than desired hardness. For example, with respect to bone segment 350, bottom surface 368 and/or top surface 370 may be shaped to achieve a desired size, introduce surface texture, a selected curvature and/or to produce a flat surface. Surface texture placed along one or more surfaces can comprise a roughened outer surface and/or an outer surface having ridges or other contours along the circumference of the bone segment. In some embodiments, processing can include creating or widening a channel through the bone plug to allow the ultimately formed implant to be inserted into a joint over a pin, or allow for the placement of a fixation screw or bolt. In some embodiments, processing can include removal of non-cortical bone material. The harvested bone plugs can be processed as described above using any variety of known methods in the art including, but not limited to, drilling, lathing, milling, sanding and the like.

Figure 20:
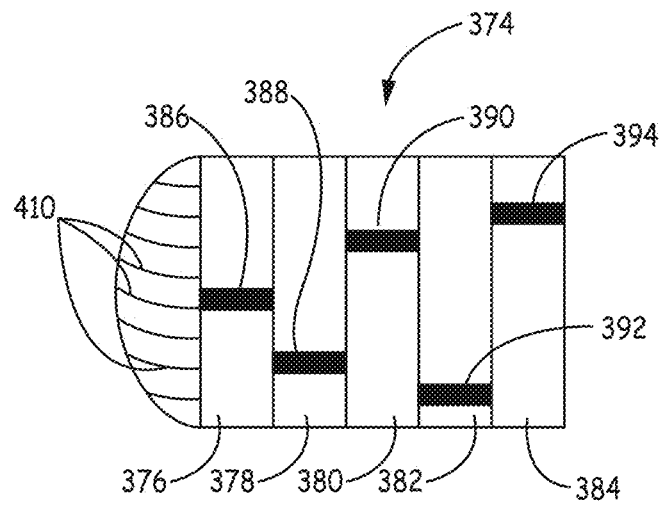
FIG. 20 is a side view of an implant having implant elements with indicia that are not aligned.
Figure 21:
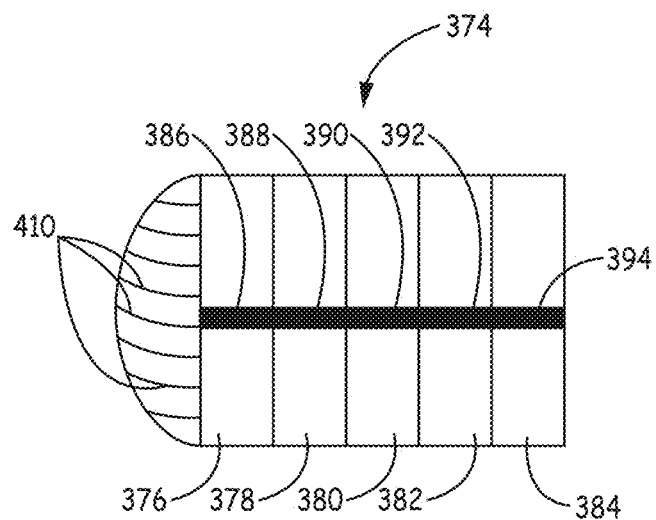
FIG. 21 is a side view of the implant in FIG. 20, reoriented so that the indicia of the implant elements are aligned.

Formation of an implant comprising stacked implant elements can comprise aligning the lamellae of the implant elements within a selected tolerance. FIGS. 20 and 21 show schematic depictions of stacked implant elements. Stacked implant 374 comprises implant elements 376, 378, 380, 382, 384 with respective indicia 386, 388, 390, 392, 394 indicating the orientation of the lamellae of the corresponding implant elements. The alignment of the lamellae of implant element 376 are represented by lines 410 (for clarity, not all lines are labeled). Referring to FIG. 20, indicia 386, 388, 390, 392, 394 are not aligned with each other, indicating the lamellae of corresponding implant elements 376, 378, 380, 382, 384 are not aligned with each other. Implant elements 376, 378, 380, 382, 384 can be re-oriented as shown in FIG. 21 so that respective indicia 386, 388, 390, 392, 394 and, therefore, the lamellae of the implant segments are aligned approximately with each other so that the strong orientation of each element can be exploited in the combined implant.

In some embodiments, the implant elements of a stacked implant can be fixedly coupled to each other using an adhesive such as surgical adhesives, including, for example, Bio-Glue® A range of approved surgical adhesives are know and are being developed, and these include, fibrin based adhesives, cyanoacrylates, albumin glutaraldehyde adhesives, collagen based products and polyethylene glycol polymers. In some embodiments, the implant elements of a stacked implant can be desirably coupled to each other through stacking alone. Implant elements having appropriately selected geometries can create desirable frictional forces between stacked elements and the bones of the joint such that the stacked implant-construct remains a substantially integrated structure within the joint or bone interface. In particular, with appropriately selected implant element geometries, the implant elements generally will not undesirably shift and/or rotate when subjected to compression forces within the joint-bone interface.

In some embodiments, the elements of a stacked implant can be coupled with a fixation screw or the like. The fixation screw can hold the implant elements in place by attaching them to host bone, holding them in uncompressed, longitudinal alignment with one another or compressing them into a stack SI Joint Procedure A variety of procedures can effectively make use of the tools and implants described herein. The procedures can be open procedures in which a larger incision is made to move tissue such that the joint (including any adjacent recess and/or the bone interface) is exposed and in view. In some embodiments of particular interest, the procedure is a less invasive procedure performed through a cannula or the like to provide more limited access to the joint through a small incision. Less invasive procedures can be desirable in some embodiments since small incisions impose less injury to the patient from the procedure and thus correspondingly may have shorter recovery times. Generally, the tools described herein are designed to facilitate the closed procedures for SI joint immobilization. Based on the teachings herein, a person of ordinary skill in the art will readily be able to adapt the tools and procedures described herein to other types of joints. The procedures are directed to immobilizing the SI joint upon a determination that such a result is indicated. Similar procedures can be performed for removing an implant from the SI joint.

In some embodiments, an implant is placed within the SI joint in contact with adjacent bone to distract the joint and to contribute to joint immobilization. In general, it can be desirable to remove at least a top layer of the native bone at the immobilization point prior to immobilization to expose an inner portion of the bone to stimulate the bone healing process that can promote bone formation at or around the implant. This exposure of the bone can be performed using drilling, cutting, scraping or the like using appropriate cutting components. Biologics, such as bone morphogenic protein, can be used to stimulate bone growth in the vicinity of the procedure, and this bone growth can contribute to fusing of the joint, which corresponds with effectively complete immobilization of the joint.

Less invasive procedures generally involve small incisions generally no more than 4.0 cm in length and in some embodiments no more than 2.5 cm across. One or multiple cuts through the tissue can be performed with scalpels or the like. The procedure can generally be organized in terms of a) locating a selected position in the joint, b) preparing the joint for immobilization and c) placement of immobilization elements. Positioning within the joint can be established using a pin or the like. Once the pin is in position, in some embodiments, a jig can be used to stabilize the location along the patient's back in the vicinity of the incision and to facilitate the introductions of instruments into the site. In some embodiments, the jig can facilitate the placement of additional implants relative to an initial implant location. In other embodiments, the procedures described herein can be desirably performed without a jig.

Based on an image of the site, pins, such as blunt pins, can be inserted to mark the edges of the joint along the patient's back. Based on the location of the marked edges of the joint, a pin can be inserted into the patient for locating the proper landmarks relative to the SI joint. A blunt pin can be used to determine the location of the SI joint more safely than the sharp pin since the blunt pin is less susceptible to accidental insertion past the joint, which can result in injury to nerves and/or blood vessels. The position of the pin can be checked with imaging, such as x-ray imaging. In some embodiments, the operating room or a nearby location can be equipped with a CT-scan or similar machine that can image the pin placement relative to the adjacent bones from a wide range of angles. Alternatively or additionally, some operating rooms are equipped with x-ray devices on a moveable arm such that images of the pin can be taken at several selected angles. With a fixed orientation x-ray apparatus, a range of angles can be imaged by moving the patient relative to the apparatus. In this way, the orientation of the pin can be verified with respect to desired placement within the joint.

In general, a set of tools can be used to facilitate the procedure for the delivery of the implant to facilitate joint immobilization. Generally, specific tools for the procedure can comprise for example, one or more pins, a sizer, cannula, drills, a driver device and various combinations thereof. Implants can be sized in diameter in a selected set of sizes so that an appropriate size can be selected based on a particular patients physical dimensions. A sizer can be used to facilitate the selection of the appropriate implant as well as to assist in the procedure by initially distracting the joint an initial amount. One or more of a cannula, drill and/or the driver can be sized correspondingly to match the selected implant size. Appropriate pins, cannula, sizers and drills are described in detail in the '238 application cited above. In some embodiments, the driving tool or impactor, such as a mallet, controls the bony implant in the implantation process, which can be controlled with a cannula and/or with a pin or threaded shaft. A driver/impactor can be cannulated with respect to appropriate components to provide for application of forces along the top surface of the implant while the implant is mounted on the pin or threaded shaft. As noted below, the tools can be packaged in a tool kit which may generally be sterilized for reuse. Implants can be separately packaged, as described further below.

Figure 22:
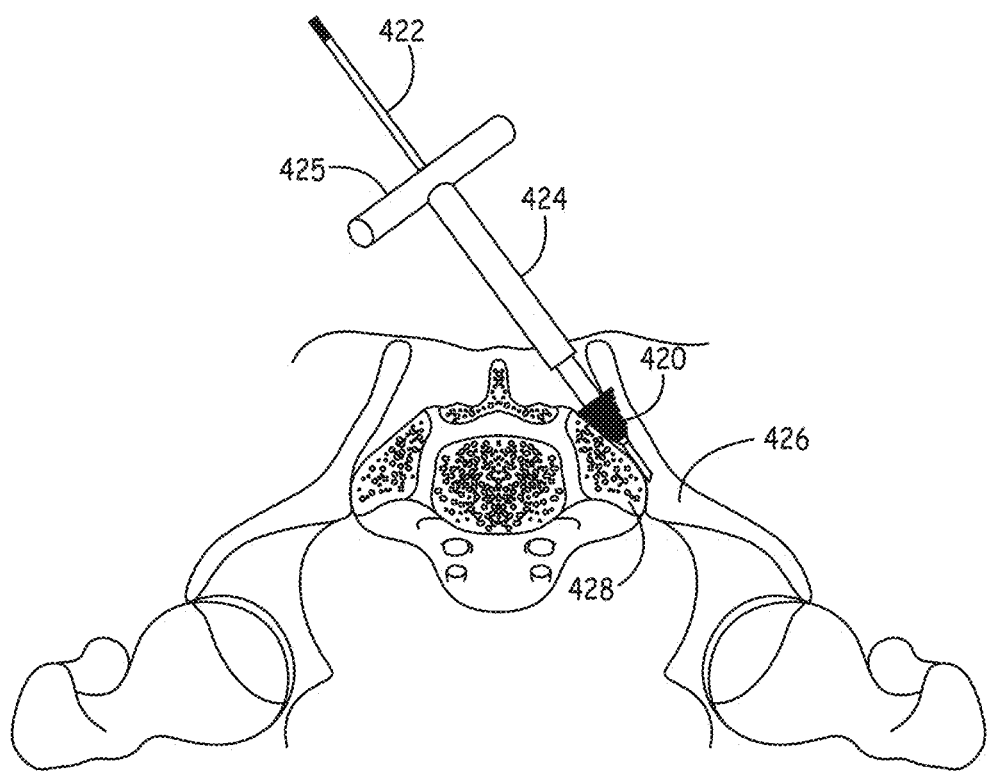
FIG. 22 is a top (inlet) view of the pelvis showing a sizer placed in a sacroiliac joint.
Figure 23A:
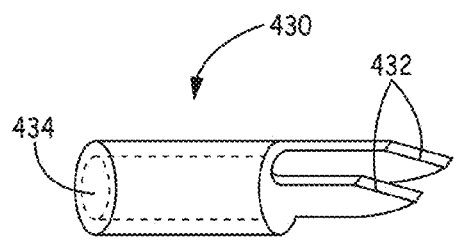
FIG. 23A is a side perspective view of a cannula having projections aligned to provide non-symmetric drilling within a sacroiliac joint.
Figure 23B:
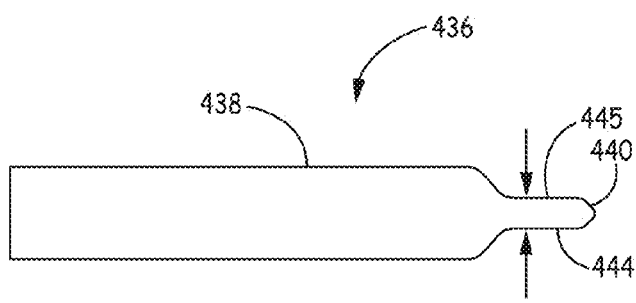
FIG. 23B is a side view of an alternative embodiment of a cannula with projections aligned to provide non-symmetric drilling within a sacroiliac joint.
Figure 23D:
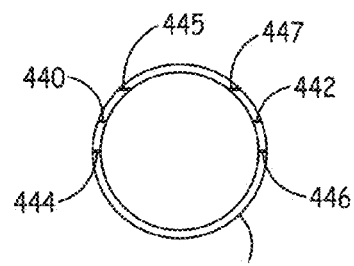
FIG. 23D is a front end view of the cannula of FIG. 23B.
Figure 23C:
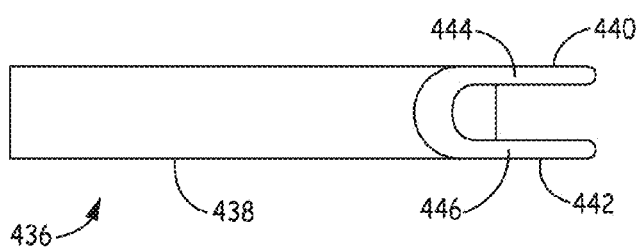
FIG. 23C is a top view of the cannula of FIG. 23B.
Figure 24:
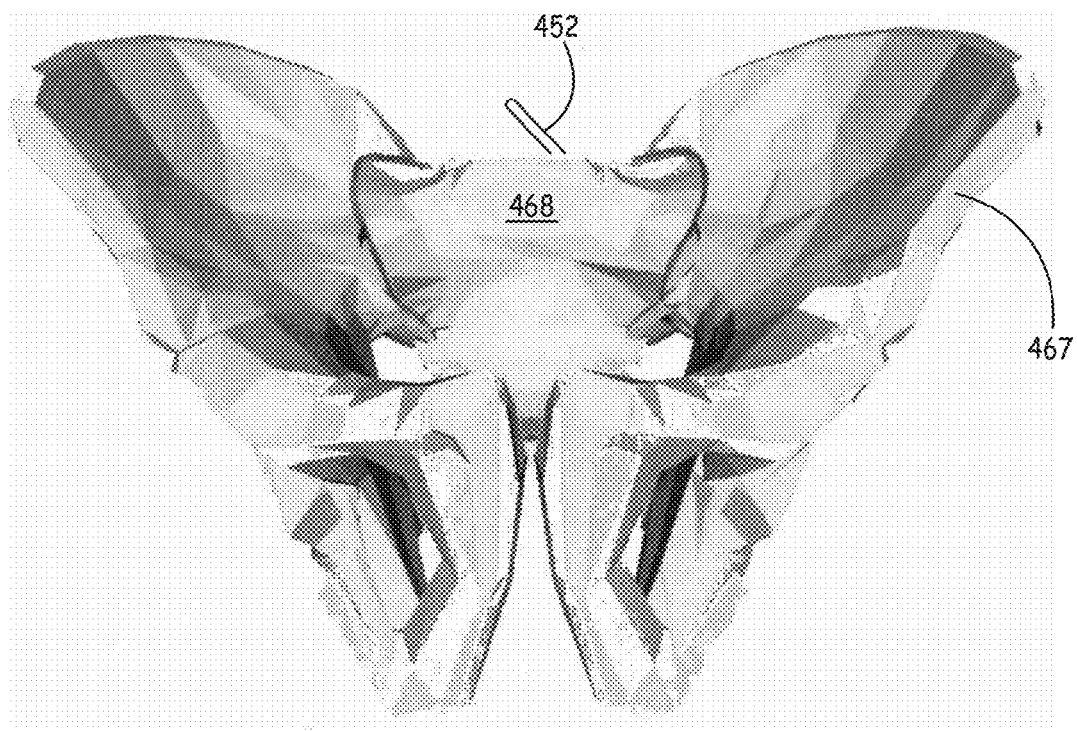
FIG. 24 is a front (antero-posterior) view of a pelvis having an implant in the sacroiliac joint.
Figure 25:
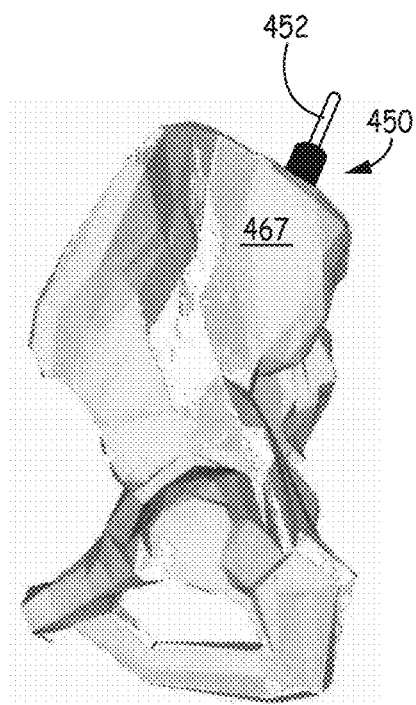
FIG. 25 is a side (left lateral) view of the pelvis and implant depicted in FIG. 24.
Figure 26:
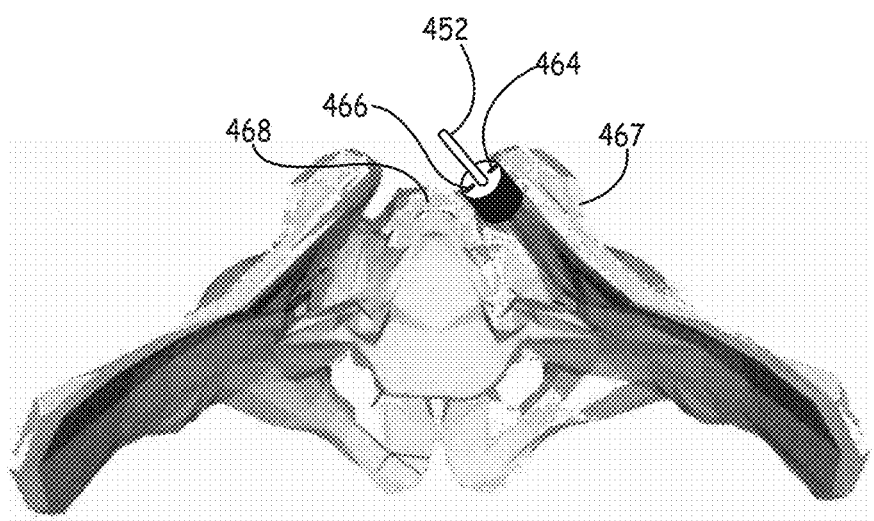
FIG. 26 is a top (inlet) view of the pelvis and implant depicted in FIG. 24.

Although optional, a sizer can be useful for sizing the SI joint using the orientation of the pin. Referring to FIG. 22, a sizer 420 is inserted over previously placed pin 422 and through the extra-articular recess and into the region of the SI joint between ilium 426 and sacrum 428. In some embodiments, an initial blunt pin is replaced after proper placement is verified, such as through x-ray imaging, with a sharp or threaded pin that can provide more stability for subsequent steps of the procedure. For example, a threaded pin can exit the recess and embed in the ilial bone 426. Sizer 420 can be smooth and tapered, or comprising threads and taper and is attached to cannulated T-handle 425. The t-handle-shaft (424) which can be used to drive sizer 420 over the pin into the joint-recess region. The sizer can be replaced with a different sized sizer if the medical professional determines that the originally selected sizer does not fit into the joint-recess region properly. Once a sizer is selected with a proper size to insert a reasonable distance into the joint with a snug feel, the sizer has established the size of the planned implant(s).

In some embodiments, one or more cannulae can be used to facilitate joint preparation and insertion of the implant element into a joint-recess region. In particular, the pin or a cannula can be used to efficiently and safely locate the joint-recess, expose a proper location in the joint, prepare the bone surfaces and provide for placement of an implant and/or other treatment/immobilization materials. An embodiment of a cannula is shown in FIG. 23, which can be particularly suited for SI joint immobilization. Cannula 430 comprises projections 432 and channel 434. In general, the cannula can be inserted over a pin through channel 434 and into a joint-recess with projections 432 sticking into and distracting the joint-recess. Tools for preparing a bone surfaces and providing for implant placement can be inserted into the joint-recess through the cannula or through the cannula and over the pin.

Improved cannulae and corresponding joint immobilization methods for joints having bones with different hardness (e.g. the SI joint) are discussed in the '238 application cited above. The '238 application also discusses the option of having nested cannula as an option for cannula size selection, but the use of individual cannula o separate sizes used individually has proven to be effective in the performance of SI immobilization procedures using a less invasive approach, but the nested cannula can be used if desired. The improved cannulae in the '238 application can have projections that are asymmetrically distributed relative to the central axis of the cannula such that when the projections are inserted into the joint, one bone of the joint (e.g. the harder bone) is drilled more than the other bone (e.g. the softer bone). While the cannula embodiment in FIG. 23A has asymmetric projections, a clearer view can be seen in the embodiment of FIGS. 23B-23D. Cannula 436 comprises generally cylindrical section 438 and projections 440, 442, which are asymmetrically placed relative to the central axis of cylindrical section 438 to provide edges 444, 445, 446, 447 in which edges 444, 446 are positioned to engage one side of the joint and edges 445, 447 are positioned to engage the other side of the joint to position the drill guide to drill one bone to a greater extent than the opposite bone.

The tools generally can have several different sized members for the size dependent components, such as the cannula, sizer, or drill bit. The different sized components generally correspond to an implant size. In this way, a health care provider can select a size of implant suitable for a patient. The implants can be provided in selected sizes with 2, 3, 4 or more than 4 optional sizes. Tool components can be reusable, and can be made from suitable materials, such as metal, including for example, stainless steel, titanium or the like.

Once the pin and sizer are positioned, the sizer can be used to guide cannula(e) into the SI joint by sliding the cannula(e) over the sizer. In some embodiments, with the cannula inserted, the blunt pin can be removed and replaced with a sharp pin that can safely go further into the joint or adjacent bone since the orientation has been confirmed. A depth guide can be used with either or both pins to limit the distance of entry of the pins into the joint. Then, the sizer can be removed.

Once the site for implant placement is localized, the site can be prepared for inserting the implant. For example, a cannulated drill bit, or the like can be used to cut into the bone around the pin position with the pin received within the channel of the cannulated drill element. The drilling procedure prepares a hole by removing soft tissue or cartilage, or otherwise decorticates the bone around the joint as a site for placement of immobilization elements. If a cannula is used during the procedure, the drill element can be inserted within the channel of the cannula. In some embodiments, the drill bit is inserted over a pin such that the drill bit is guided by the pin (if no cannula is used) or both the pin and the cannula (if a cannula is used). In some embodiments, the drill bit can have a bushing or the like to steady the drill bit within the cannula. A motorized drill can replace a manual drill design if desired.

The desired implant can then be placed in the SI joint-recess at the pin position by sliding the implant over the pin and/or within the channel of a cannula. While the implant is positioned for placement, the implant can be oriented so that the lamellae are aligned across the joint (i.e. between the sacrum bone and ilium bone for SI joint immobilization), before the implant is delivered into the prepared region of the joint. With the lamellae oriented across the joint, the stability of the implant is improved relative to embodiments in which the lamellae are oriented differently. The orientation of the lamellae can be determined by visual inspection of the indicia. Generally, a joint is prepared to tightly receive the implant, and the implant cannot be easily reoriented once inserted into the prepared region. Correspondingly, orienting the lamellae of the implant prior to insertion into the prepared region can facilitate implantation. While the joint can be distracted by projections from the cannula, the implants are still generally tightly fitting within the prepared implant position in the joint. While it may be possible to manually push the implant or the individual elements of the implant into the joint, a hammer or the like may be helpful to drive the implant element(s) into position. The driver should engage the implant element in such a way to distribute the force approximately evenly and reduce chances of cracking the bone element.

For stacked implants, the implant elements can be inserted into the prepared area of a joint sequentially, simultaneously, in partial groups or a combination groups and individual elements. In embodiments involving sequential placement of individual elements, each implant element can be oriented using visual inspection of indicia such that the lamellae are generally aligned across the joint before being inserted into the prepared area of the SI joint. The implant elements are inserted in an order to reproduce the desired implant structure within the joint. The implants may be shaped, ridged, or notched to interact with one another, or the receiving bed in the patient, to retain alignment and resist loss of orientation. In some embodiments, a stacked implant can be inserted into a joint as whole by aligning the lamellae of the stacked elements and, subsequently, inserting the implant into the prepared joint area. FIGS. 24-27 show a schematic depiction of an embodiment of a stacked implant inserted into a SI joint-recess. Referring to the figures, stacked implant 450 is inserted over pin 452 and into the SI joint between ilium 467 and sacrum 468. Stacked implant elements 454,468,458,460, 462 have lamellae, represented by lines 462 (for clarity, not all lines are numbered), that are aligned across the SI joint-recess. The indicia on the implant elements 468,458,460, 462 (not shown) are aligned with indicia 464,466 for implant element 454.

Figure 27:
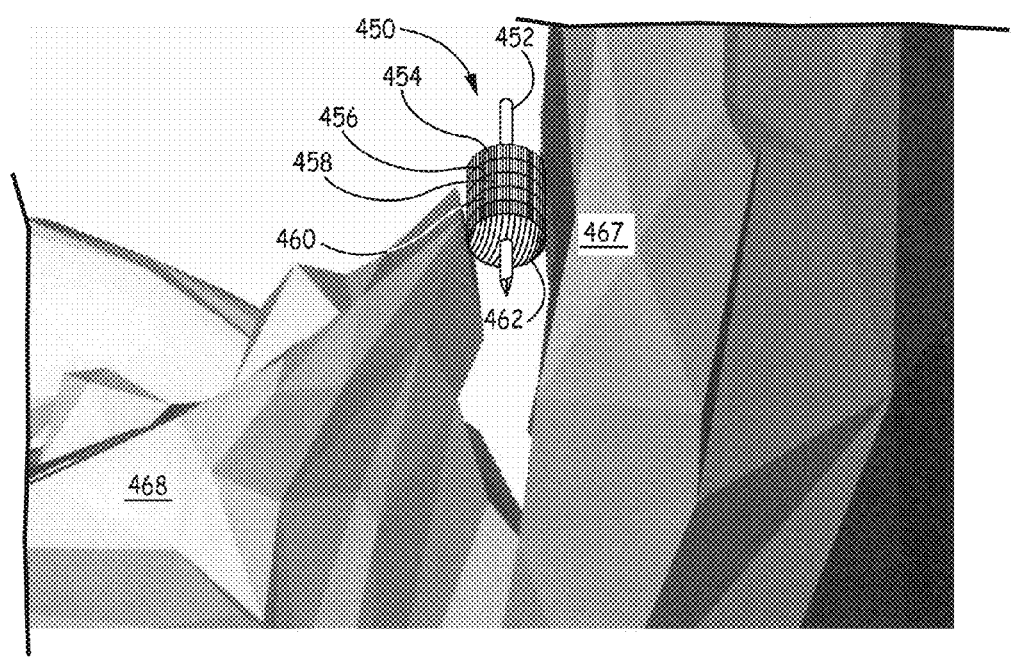
FIG. 27 is a perspective view of the pelvis and implant depicted in FIG. 24.
Figure 28:
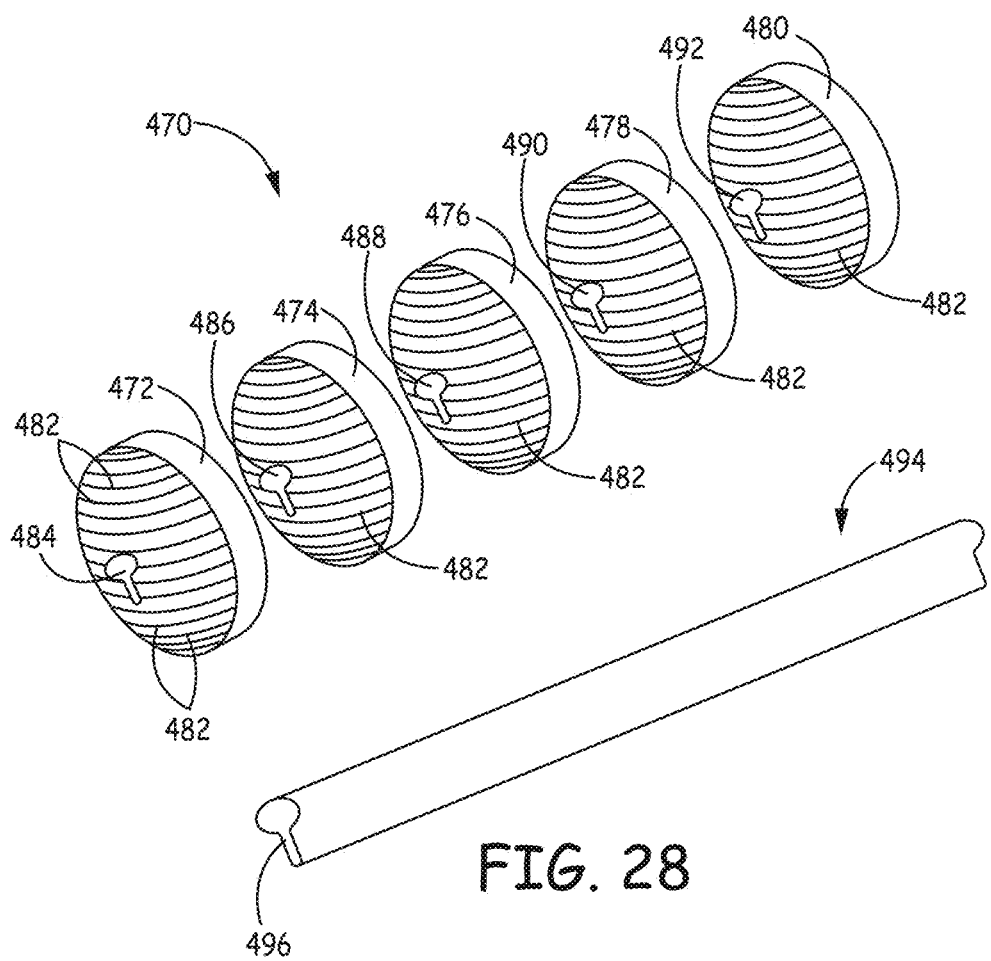
FIG. 28 is a perspective view of an implant having implant elements with non-cylindrical channels and a pin with a matched cross sectional shape to form a lock and key relationship.
Figure 29:
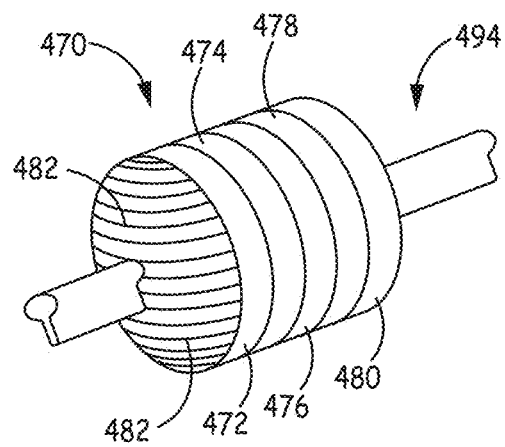
FIG. 29 is a perspective view of the implant elements of FIG. 28 aligned on the pin of FIG. 28.

In some embodiments, the use of implants with a non-cylindrical channel and a pin with at least a portion of the pin being contoured with a non-circular cross section to match the channel can facilitate alignment of the implant prior to or during insertion into a joint. Referring to FIG. 28, implant 470 comprises implant elements 472, 474, 476, 478, 480 having lamellae aligned as indicated by lines 482 (for clarity, not all lines are numbered). Implant elements 472, 474, 476, 478, 480 can have non-cylindrical channels 484, 486, 488, 490, 492 that serve both as a channels through the respective implant elements as well as indicia indicating the alignment of the lamellae, although other visible indicia can also be used as described above. Non-cylindrical channels 484, 486, 488, 490, 492 are sized to fit over pin 494 with non-circular cross section 496, as shown in FIG. 29. Pin 494 aligns channels 484, 486, 488, 490, 492 so that the lamellae of the respective implants are aligned. Implant elements 472, 474, 476, 478, 480 can be delivered over pin 494 into the prepared region of the SI joint sequentially as a stack. If a non-notched pin is already inserted into the joint, the pin can be removed and replaced with a notched pin for alignment of the implant elements. While FIGS. 27 and 28 show a particular lock and key shapes for a pin and implant channels, other shapes can be used as desired, such a pin with a flat edge machined into a cylindrical pin with corresponding channels placed through the implant.

In another embodiment the shape of the central channel, or of the bone elements approximating surfaces may allow or encourage obliquity of the individual bone element, under the compression of a fixation screw resulting in a irregular, notched, or rasp-like surface.

Tools generally can be formed from suitable material, such as materials that can be subjected to repeat sterilization procedures without excessive material fatigue. Suitable materials include, for example, metal, such as stainless steel, ceramics or the like.

Fixation screws may be of preferred biologic and mechanical properties, including stainless steel, titanium, titanium alloys, tantalum, ceramic materials, such as synthetic bone-like materials, for example, hydroxyapatite, and the like. Screw-like or cylindrical implants to maintain alignment are also contemplated in the shape of cylinders or tapered, cylindrically symmetric elements.

Once the lamellae are oriented as desired, the implant can be delivered into the prepared region of the SI joint, for example, by delivering individually as a single bone implant, a stack of associated but unfixed bone implants, or a fixed bone implant-construct. This may be accomplished by delivery through a preplaced cannula, by twisting, rotating, pushing or by hammering. The implant elements can be delivered singly, in groups of two or more, or as a stacked implant. In some embodiments, a driving tool can be used to place an element(s) or implant in the SI joint along a threaded shaft or pin. In another embodiment, a cannulated driver-impactor can operate over a pin, allowing the elements(s) or implant to slide into place. In some embodiments the driving instrument can be adapted to disperse driving forces evenly through the implant, for example, by matching the curve or shape of the driving instrument with that of the implant. In such embodiments, the risk of fracture or other damage to the element(s) or implant can be reduced, relative to a driving instrument have a non-matched geometry.

Optionally, a syringe with filler material and/or biologics can be inserted over the pin or following removal of the pin, and into the SI joint to apply material into the passageway, such as after the immobilization element is delivered. In some embodiments, the syringe can have a channel for delivery over the pin. The pin may or may not be removed following the delivery of the immobilization element and/or filler material. In some embodiments, the pin may be cut down if desired. Following deployment of the immobilization element(s) and any additional treatment materials, the incision is then closed.

A series of implants can be placed along the joint using either an open procedure or a set of less invasive procedures. For example, the series of immobilization elements can be placed in a row in the joint-recess. In this way, two, three, four or more immobilization elements can be placed along the SI joint-recess. In some embodiments, the jigs discussed above can be used to place multiple pins and/or cannulated tools into the SI joint-recess.

The procedure described above can be adapted for removing or extracting an implant from a joint-recess, e.g., the SI joint. To perform the removal procedure, a guide pin can be placed within the implant in the joint. Imaging can be used to locate the implant in the joint to guide the insertion of the pin within the implant. A sizer, depth guide, and sharp pin can be used if desired to obtain proper placement of the pin. One or more cannula can be inserted into the joint so the cutting components can accurately access the implant in the joint. For example, a cannulated drill can be used to drill within the cannula and into the implant and drilling away the implant. Alternatively, the cutting components can be used to create a passageway near and/or within the implant, and the cutting components can be used to release the implant. After the implant is removed, a different implant or no implant can be placed in the same or different location. Regardless, the passageway created into the SI joint-recess can be filled with a filler material using a syringe if desired, following removal of the implant.

Packaging

The tools described above can be distributed in a kit for use by a medical professional. Kits provide a convenient and efficient approach to the distribution of equipment for the performance of a selected embodiment of the procedure. Combinations of tools for a particular procedure can be conveniently arranged in a kit such that tools to be used together are available to the physician/health care professional performing the procedure. These tools may be sold individually, as a set with certain selected tools, or together with all the tools. However, selected tools may be sold together as assembled by the manufacture or vendor or selected in a customized fashion by the consumer. For example, the implant and/or alignment components can be sold as an accessory separately from the kit and from each other. For stacked implants, a package can comprise a unitary implant comprising the assembled implant elements or a package can comprise un-assembled implant elements, which can be packages individually to provide for choice in the length of the assembled implant or in groups to provide a particular length overall.

Figure 30:
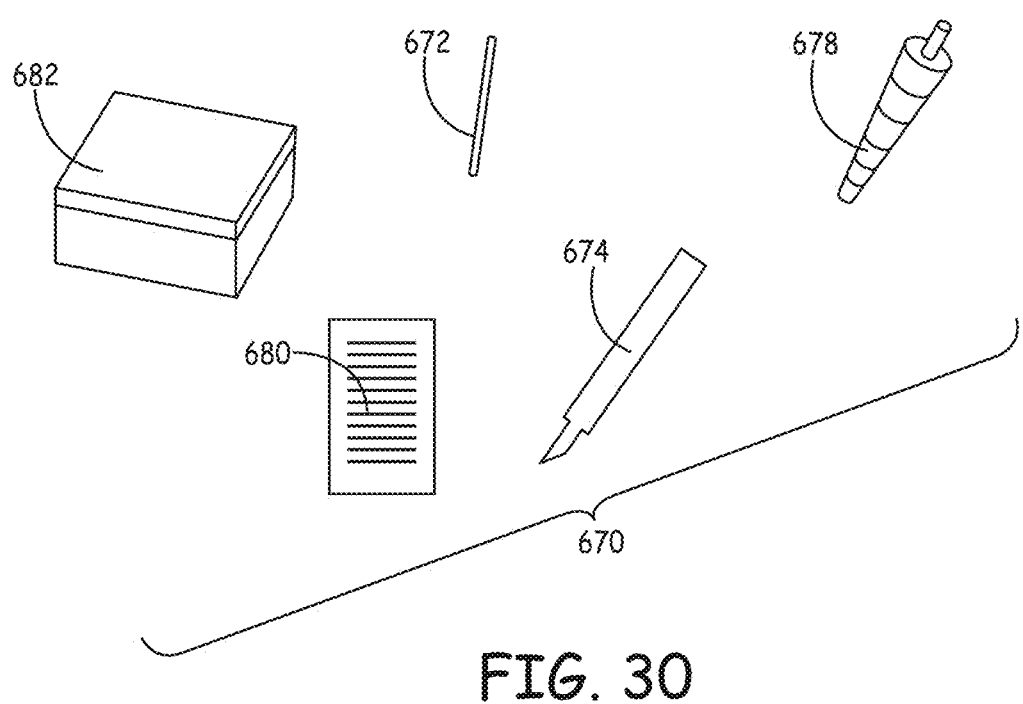
FIG. 30 is a schematic depiction of an implant kit.

Generally, the kit can be distributed with the tools in a container. The tools can be sterilized prior to use. The tools are generally reused. Recycled/reusable components are generally formed from a material, such as described above, that can be subjected to an appropriate sterilization approach without damage components are generally formed from a material that can be subjected to an appropriate sterilization approach without damage. A kit comprising the collection of tools along with appropriate labels in a container is shown schematically in FIG. 30. Specifically, kit 670 comprises pin 672, cannula 674, drill bit 678 and optionally instructions with appropriate warnings 680 within container 682. Various other optional components can be included with the kit to facilitate access to the implant point, preparation of the implant site and/or delivery of the implant.

In some embodiments, the implant and/or alignment components are sold separately from the tools and each other. The containers holding implant can have a sterile interior. The sterilization can be performed by any approach in the art, which can be based, for example, on radiation, chemicals and/or sterile process. Clearly, implants are generally left with the patient and are not reused.

Each of these kits (e.g. kits with selected tools, kits with alignment components, kits with implants, etc.) can also include appropriate instructions, warnings, and/or labeling.

The embodiments above are intended to be illustrative and not limiting. Additional embodiments are within the claims Although the present invention has been described with reference to particular embodiments, workers skilled in the art will recognize that changes may be made in form and detail without departing from the spirit and scope of the invention. The incorporations by reference above are intended to incorporate the full disclosures of the references to the extent that the incorporated subject matter is not inconsistent with the explicit disclosure herein, which will not be altered by any incorporation by reference, as well as to incorporate the disclosures with respect to the specific issues referenced in the incorporation.

What is claimed is:

1. A bone implant element comprising a harvested and processed cortical bone graft with any soft bone removed having a generally cylindrical longitudinal shape along a cylindrical axis, a concave bottom surface and a visual indication of the lamellae orientation of bone material wherein the lamellae are oriented approximately parallel with respect to planes perpendicular to the cylindrical axis.

2. The bone implant element of claim 1 wherein the implant has a convex upper surface.

3. The bone implant element of claim 1 wherein the bottom surface is curved in one dimension and approximately uncurved in an orthogonal dimension.

4. The bone implant element of claim 1 wherein the implant has a tapered side surface.

5. The bone implant element of claim 1 comprising a central channel extending through the implant between a top surface and the bottom surface.

6. The bone implant element of claim 5 wherein the central channel is generally cylindrical.

7. The bone implant element of claim 1 comprising an anti-rotation-notch in its side surface.

8. The bone implant element of claim 1 comprising texture or ridges.

9. The bone implant of claim 8 wherein the implant is chemically etched or has a coating material.

10. The bone implant element of claim 1 wherein the visual indication is on a side surface of the implant element.

11. The bone implant element of claim 1 wherein the visual indication is on the bottom surface.

12. A method for making a bone implant element, the method comprising:
    machining a surface of a generally cylindrical bone plug cut from the wall of a long bone to form a concave surface with cortical bone with lamellae oriented approximately planar according to a plane perpendicular to the cylindrical axis; and marking the orientation of lamellae in the bone to form a bone implant element of claim 1.

13. The method of claim 12 wherein the marking comprises forming a visual indication on a side surface of the bone plug and/or a top surface of the bone plug.

14. The method of claim 12 wherein the marking comprises forming a distinctive shape that provides a corresponding orientation of lamellae through orientation of the shape.

15. The method of claim 12 comprising machining the bone plug to form a channel through the bone plug between a top surface and a bottom surface.

16. The method of claim 12 comprising machining a side, top or bottom surface of the bone plug to form a textured side surface, top surface, bottom surface, combinations thereof or portions thereof.

17. The method of claim 12 comprising machining a side surface of the bone plug to form a tapered bone element.

18. A bone implant comprising a plurality of nested, harvested and processed bone elements wherein the top surface of a first element stably engages a bottom surface of a second element with lamellae of the first element aligned within about 20 degrees of lamellae of the second element.

19. The bone implant of claim 18 wherein the implant has a generally cylindrical longitudinal shape.

20. The bone implant of claim 18 wherein a plurality of elements have side surfaces that align to form a non-cylindrical side surface when the implant is compressed along a long axis with longitudinal forces.

21. The bone implant of claim 18 wherein the bone elements comprise a visual indication on a side surface indicating the alignment of the lamellae within the bone element.

22. The bone implant of claim 18 wherein the bone elements comprise a visual indication on a bottom surface indicating the alignment of the lamellae within the bone element.

23. The bone implant of claim 18 wherein the bone elements have a top surface that is convex and a bottom surface that is concave.

24. The bone implant of claim 18 wherein the bone elements have a top surface that is convex in one direction and approximately un-curved in an orthogonal direction and a bottom surface that is concave in the one direction and approximately un-curved in the orthogonal direction.

25. The bone implant of claim 18 wherein the bone elements comprise a channel and wherein the channels are aligned to form a passageway through the implant.

26. The bone implant of claim 18 wherein the lamellae are oriented approximately planar with respect to planes perpendicular to the cylindrical axis.

* * * * *